United States Patent
Brayanov et al.

(10) Patent No.: US 12,048,526 B2
(45) Date of Patent: Jul. 30, 2024

(54) DEVICES AND METHODS OF CALCULATING AND DISPLAYING CONTINUOUSLY MONITORED TIDAL BREATHING FLOW-VOLUME LOOPS (TBFVL) OBTAINED BY NON-INVASIVE IMPEDANCE-BASED RESPIRATORY VOLUME MONITORING

(71) Applicant: Respiratory Motion, Inc., Watertown, MA (US)

(72) Inventors: Jordan Brayanov, Medford, MA (US); Jenny Freeman, Weston, MA (US); Brian Harvey, Cambridge, MA (US); Chunyuan Qiu, Huntington Beach, CA (US); Man Ching Cheung, Arlington, MA (US); Jasmin Imsirovic, Cambridge, MA (US)

(73) Assignee: Respiratory Motion, Inc.

( * ) Notice: Subject to any disclaimer, the term of this patent is extended or adjusted under 35 U.S.C. 154(b) by 402 days.

(21) Appl. No.: 16/222,783

(22) Filed: Dec. 17, 2018

(65) Prior Publication Data
US 2019/0183383 A1    Jun. 20, 2019

Related U.S. Application Data

(60) Provisional application No. 62/599,153, filed on Dec. 15, 2017.

(51) Int. Cl.
*A61B 5/08* (2006.01)
*A61B 5/00* (2006.01)
(Continued)

(52) U.S. Cl.
CPC .......... *A61B 5/0809* (2013.01); *A61B 5/0803* (2013.01); *A61B 5/085* (2013.01);
(Continued)

(58) Field of Classification Search
CPC ..... A61B 5/0809; A61B 5/0803; A61B 5/085; A61B 5/742; A61B 5/0826; A61B 5/091;
(Continued)

(56) References Cited

U.S. PATENT DOCUMENTS

| 2001/0004893 A1* | 6/2001 | Biondi | A61M 16/0051 |
|---|---|---|---|
| | | | 128/204.18 |
| 2008/0077033 A1* | 3/2008 | Figueiredo | G16H 40/63 |
| | | | 600/529 |

(Continued)

FOREIGN PATENT DOCUMENTS

| JP | 2012187292 A | 10/2012 |
|---|---|---|
| JP | 2016179187 A | 10/2016 |

(Continued)

OTHER PUBLICATIONS

Bardoczky, G.I. "Continuous Spirometry: An Aid to Monitoring Ventilation During Operation", British Journal of Anaesthesia; 71, p. 747-751. (Year: 1993).*

(Continued)

*Primary Examiner* — Andrey Shostak
(74) *Attorney, Agent, or Firm* — Remenick PLLC

(57) ABSTRACT

Methods and systems of displaying flow-volume loops of a patient and variability of the flow-volume loops across measured breaths are disclosed. The methods comprise obtaining a physiological dataset of the patient on a data acquisition device, applying a smoothing and curve fitting algorithm to the physiological dataset on a processing device to obtain real-time volume and flow data at a plurality of time instances, applying a visualization algorithm on the processing device to the volume and flow data to create a series of flow-volume loops based on the volume and flow data, and outputting a plot of the flow-volume loops on a display device to aid evaluation or diagnosis of the patient.

54 Claims, 9 Drawing Sheets

DIAGRAM REPRESENTATION:
FLOW-VOLUME LOOP BECOMES DENSER AND MORE COMPACT AS RESPIRATION RATE INCREASES

(51) Int. Cl.
*A61B 5/085* (2006.01)
*G16H 40/63* (2018.01)
*G16H 50/20* (2018.01)
*G16H 50/30* (2018.01)
*A61B 5/091* (2006.01)

(52) U.S. Cl.
CPC ............. *A61B 5/742* (2013.01); *G16H 40/63* (2018.01); *G16H 50/20* (2018.01); *G16H 50/30* (2018.01); *A61B 5/0826* (2013.01); *A61B 5/091* (2013.01)

(58) Field of Classification Search
CPC ....... A61B 5/7264; A61B 5/743; A61B 5/746; A61B 5/7465; G16H 50/30; G16H 50/20; G16H 40/63
See application file for complete search history.

(56) References Cited

U.S. PATENT DOCUMENTS

| | | | | |
|---|---|---|---|---|
| 2010/0222693 A1* | 9/2010 | Eriksen | ................ | A61B 5/087 600/538 |
| 2011/0286652 A1 | 11/2011 | Kabus et al. | | |
| 2012/0215504 A1 | 8/2012 | Parker et al. | | |
| 2012/0221971 A1* | 8/2012 | Trotta | ................ | G06F 3/0482 715/803 |
| 2014/0012150 A1* | 1/2014 | Milne | ............... | A61M 16/0051 600/529 |
| 2015/0073281 A1* | 3/2015 | Mestha | ................ | A61B 5/091 600/473 |
| 2016/0367186 A1* | 12/2016 | Freeman | ............... | A61M 5/168 |
| 2017/0100059 A1* | 4/2017 | Kao | .................... | A61B 5/6823 |

FOREIGN PATENT DOCUMENTS

| | | | | |
|---|---|---|---|---|
| WO | WO02069878 A | | 9/2002 | |
| WO | WO-2015148169 A1 * | | 10/2015 | ........... A61B 5/7264 |

OTHER PUBLICATIONS

Lionetti, Vincenzo, et al. "Impact of acute changes of left ventricular contractility on the transvalvular impedance: validation study by pressure-volume loop analysis in healthy pigs." PLoS One 8.11: e80591. (Year: 2013).*

PCT Search Report and Written Opinion for PCT App. No. PCT/US18/066060, Dated Jun. 25, 2020.

Japanese Office Action for Japanese Patent Application No. 2020-552683, Dated Dec. 1, 2022.

* cited by examiner

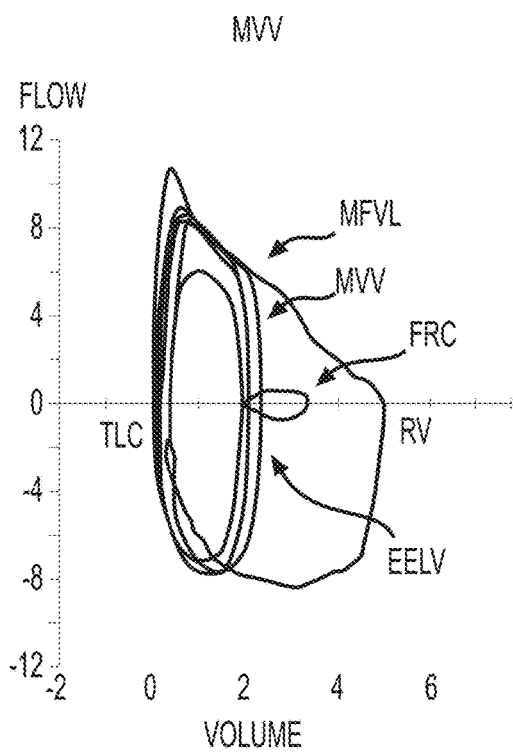 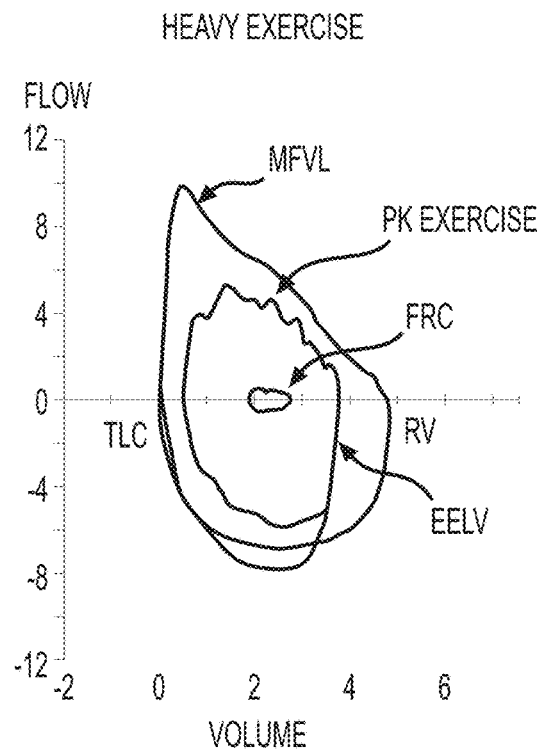
FIG. 3A
FIG. 3B

GUI BASED NOTIFICATION: 2-DIMENSION METHOD OF ALERTING USER WHEN FLOW-VOLUME LOOPS ARE OUT OF PREDETERMINED RANGE.

RANGES DETERMINED BY USER OR BY ALGORITHM
▭ FVL WITHIN RANGE
▰ FVL OUT OF RANGE
→ TIME

GUI BASED NOTIFICATION: 3-DIMENSION METHOD OF ALERTING USER WHEN FLOW-VOLUME LOOPS ARE OUT OF PREDETERMINED RANGE.

DEVICES AND METHODS OF CALCULATING AND DISPLAYING CONTINUOUSLY MONITORED TIDAL BREATHING FLOW-VOLUME LOOPS (TBFVL) OBTAINED BY NON-INVASIVE IMPEDANCE-BASED RESPIRATORY VOLUME MONITORING

REFERENCE TO RELATED APPLICATIONS

This application claims priority to U.S. Provisional Application No. 62/599,153, filed Dec. 15, 2017, of the same name, the entirety of which is specifically incorporated by reference herein.

BACKGROUND

1. Field of the Invention

The present invention is directed to devices and methods of calculating and displaying continuously monitored tidal breathing flow-volume loops (TBFVL or FVL) obtained by non-invasive impedance-based respiratory volume monitoring.

2. Description of the Background

Real time flow-volume loop monitoring is useful in diagnosis, differential diagnosis, monitoring and treatment responsiveness of certain lung diseases, however its clinical use in non-intubated and tidal volume breathing patients has been limited because of technological difficulties.

Spirometry is an integrated part of pulmonary function testing, in which various parameters of lung functional status are measured and presented, such as Tidal Volume (TV), Functional Residual Capacity (FRC), Lung Capacity (LC), etc. (see table 1). Although spirometry is the gold standard for flow-volume loop measurement in non-intubated patients, the tidal breathing flow-volume loop (TBFVL or FVL) can provide useful information that traditional spirometry cannot. Spirometry tests typically need awake, alert, and cooperative patients. The maneuvers required to collect spirometry data typically have a learning curve for the patient or individual and require spirometry tests for a given maneuver to be within +/−3% to be considered acceptable. Children, older adults, and persons with diseases affecting cognitive function, inspiratory/expiratory muscle strength, and lung disease (i.e. delirium, dementia, COPD, amyotrophic lateral sclerosis, etc.) require substantial training, practice and coaching to achieve quality results. Often usable results are unobtainable. By removing the requirement for patient cooperation or making significant respiratory effort, TBFVL measurements also have the advantage of providing data demonstrating the respiratory function under the baseline conditions or under conditions of altered physiology such as exercise or disease state, or before and after the delivery of medication or other therapy.

TABLE 1

| Pulmonary Function Test | Instrument | Measures | Function |
|---|---|---|---|
| Spirometry | Spirometer | Forced vital capacity (FVC) | Volume of air that is exhaled after maximum inhalation |
| | | Forced expiratory volume (FEV) | Volume of air exhaled in one breath |
| | | Forced expiratory flow, 25-75 percent | Air flow in the middle of exhalation |
| | | Maximum voluntary ventilation (MVV) | Volume of air that can be inspired and expired in 1 minute |
| | | Slow vital capacity (SVC) | Volume of air that can be slowly exhaled after inhaling past the tidal volume |
| | | Functional residual capacity (FRC) | Volume of air left in the lungs after normal expiration |
| | | Residual Volume (RV) | Volume of air in the lungs after maximum exhalation |
| | | Total lung capacity (TLC) | Maximum volume of air that the lungs can hold |
| | | Expiratory reserve volume (ERV) | Volume of air that can be exhaled beyond normal exhalation |
| | | Minute ventilation (MV) | Volume of air exchanged in 1 minute during normal breathing |
| Gas Diffusion | Blood gas analyzer | Arterial blood gases | Concentration of oxygen and carbon dioxide in the blood |
| | | Delivery of oxygen (DO2) | Rate of oxygen delivered to tissues; calculated as [cardiac output × arterial O2 content × 10]. |
| | | Delivery of oxygen (based on cardiac index, DO2I) | Rate of oxygen delivered to tissues; calculated as [cardiac index × arterial O2 content × 10]. |
| | | VO2 | Peak oxygen utilization |
| | | MV/VCO2 slope | Minute ventilation (MV) to exhaled carbon dioxide (VCO2) ratio |
| | | PaCO2 | Arterial carbon dioxide partial pressure |

Increasing evidence indicates dynamic changes in TBFVLs in spontaneously breathing patients, either awake or asleep, has clinical significance for both normal patients and for patients with either restrictive or obstructive airways. However, lack of monitoring in the field limits the use of this information.

Recently, several non-invasive methods have been developed to fill the technological gap necessary for clinical monitoring, including vest- and mask-based systems. FloRight, a vest-based system, measures thoracoabdominal volume by detecting magnetic field changes in flexible coils worn by the patient. While this method is non-invasive, studies have concluded that it is not suitable for tidal volume measurements or long term monitoring. Comparison between FloRight and a spirometer showed that FloRight consistently underestimated tidal volumes. The FloRight system also requires repeated drift correction of the volume signal, which can influence measurements over the long term. A mask-based system using an ultrasonic flowmeter (USFM) replaces the mouthpiece from a standard PFT with a facemask. The USFM uses ultrasound based measurements of air flow that can be more accurate than vest-based volume measurements; however, it is not without its limitations. The intrusiveness of the facemask restricts the device to spot checks of tidal volume and minute ventilation, and in turn prevents continuous long-term monitoring. The face mask also adds additional dead space which can alter breathing pattern and depth.

Non-invasive respiratory monitoring systems have been applied to monitor patients with lung disorders including asthma, COPD, and others. Expiratory flow-limitation can be observed in flow-volume loops for obstructed patients, particularly those with severe cases of obstructive disease in both standard FVL based on maximum inhalation as well as TBFVL (see FIG. 3C). A technique called negative expiratory pressure (NEP) has been applied in conjunction with a spirometer to determine if a patient has expiratory flow-limitation during tidal breathing. The technique works by applying a small negative pressure during the expiratory phase of a tidal breath, which increases expiratory flow. The flow-volume loop deviates from the original TBFVL when NEP is applied to patients with tidal flow limitation, but the expiratory curve remains the same in patients with tidal flow limitation. This technique can only be performed in patients with a mouthpiece and requires a vacuum. As a result of practical limitations and lack of commercial technological solutions, the technique has not been widely implemented in clinical practice.

TBFVLs have also been measured in healthy individuals in the field of exercise physiology. It is documented that some individuals, including trained athletes, exhibit flow-limitation during exercise. However, these measurements have all been collected in a controlled laboratory environment with specialized equipment. In particular, spirometers that use nose clamps and mouthpieces or facemasks, can only be used for a limited amount of time. This prevents continuous monitoring of athletes or other individuals during rest and recovery periods following specialized exercise trials with respiratory monitoring equipment.

TBFVLs have been of interest in veterinary medicine since animals cannot be trained to preform pulmonary function tests. Similar to human athletes, the ability to measure respiratory function in racing animals, equestrian sports, and others can be useful for treating animals and maximizing performance. USFM have been used to measure TBFVLs in sporting horses in order to detect recurrent airway obstruction. Other veterinary applications are similar to human medicine for diagnosis, monitoring or evaluation of efficacy of therapeutics.

Thus, there is a need for a system that can monitor tidal breathing flow-volume in real time, noninvasively, and continuously up to 24 hours or longer. Since breath size and rate will influence what is measured in the TBFVL, incorporation of these parameters would be useful for some applications. Accurate monitoring of TV and RR as well as TBFVL would assist in interpretation of the data.

SUMMARY OF THE INVENTION

The present invention overcomes the problems and disadvantages associated with current strategies and designs in providing devices and methods for collecting and displaying a respiratory volume trace, obtained by a non-invasive respiratory volume monitor, in graphical form in which instantaneous respiratory volume (V) is plotted along one axis and changes in respiratory flow (i.e. the change of respiratory volume as a function of time, dV/dt) is plotted along a second axis. Pairing this graphic with other physiologic parameters such as TV, RR, and inspiratory-to-expiratory ratio provides additional information.

Additional embodiments and advantages of the invention are set forth, in part, in the description which follows and, in part, may be obvious from this description or may be learned from the practice of the invention.

The embodiments of this present invention enable data to be collected and analyzed by computer software to provide TV and RR data, in order to generate and display numerical values, plots, and traces that can be presented to users at the locations of their choosing, including at the point of care or source of measurement of an individual or at a remote location. The custom computer software code can reside on a computer processing and storage unit internal to the measuring apparatus or located externally and can perform calculations and computer operations on measurements derived from electrodes or other sensors which may have preferred positioning on the human body. The combination of the measurement apparatus and computer software preferably enables presentation of the traces, TBFVL, and numerical indices for respiratory status, with the entire collection of numerical indices and plots becoming a "respiratory profile" or "respiratory signature" that describes the patient. The invention can also generate maximum effort TBFVL by having the subject or patient breath in that prescribed manner.

The present invention can provide flow-volume loop (FVL) measurements, whether they are from maximal effort or from continuous tidal breathing monitoring, or whatever breathing pattern as proscribed by diagnosticians. The present invention applies to measurements of all forms of respiration for which an FVL can be generated.

In one embodiment, the present invention preferably enables the collection of respiratory measurements from many patients, allowing for the continuing incorporation of new data for extension and refinement of existing profiles and signatures calculated by custom software. There are features in the computer software code that are common to all embodiments summarized and described in detail herein.

In one embodiment, the present invention preferably allows for concurrent collection of respiration monitoring and absolute volume and flow information, enabled by the software. In a preferred embodiment, this is associated with a preferred positioning of measurement electrodes.

In one embodiment, impedance measurements from a set of electrodes or sensors are recorded and transmitted to a computer processing unit and converted into a volume trace and numerical values that describe the respiratory status of a patient. In a preferred embodiment, the current invention provides this information with plots that show the relationship between instantaneous changes in both volume and flow rate in time (i.e. TBFVL) and associated new information derived from these plots. In one embodiment new information is preferably generated by custom software programs that make calculations using the TBFVL.

In one embodiment the shape of the FVL is interpreted by a physician, physiologist or other user who can use the FVL shape to diagnose or assist in the diagnosis of disease, assess physiology, monitor or assess response to therapy. The invention will allow for short-term and long-term monitoring (hours to days to weeks to even longer periods) with repeated application of new electrodes. The TBFVL shape data can be used to assess patients with restrictive or obstructive pulmonary disease, cardiac disease with pulmonary sequelae, effects of exercise or training, and effects of drugs or device driven therapy or methods of improving or maintaining health. In a preferred embodiment, the software code decomposes the FVL into segments for calculations and automated data fitting and each segment is fitted with a different mathematical function. In one embodiment, these generated data points are evaluated for fit and consistency in data and may be further refined into numerical parameters that describe the feature. These features preferably identify aspects of the respiratory cycle for each individual breath, and enable tracking of these same features over time to create trends of the observed breathing patterns, or "trajectories", for a single patient. Because of the large amount of numerical values or metrics created for each breath for the entire monitoring period, for even a single patient, these trends can be summarized by the computer software code to create a "profile" of the respiratory status of the patient.

These profiles can further be refined and classified according to their association and appearance with different pathological presentations and patient histories. In one embodiment, the software separates the classification into profiles and then classifiers of profiles preferably using both supervised and unsupervised algorithms. While the supervised algorithms preferably use statistical tools and projections into abstract phase space to identify groupings, unsupervised learning algorithm will preferably take advantage of deep-learning machine learning tools using additional dedicated computational processing units. The principle is that each FVL is a 2-dimensional plot, which is a 2-dimensional image and many FVLs plotted in time would create a 3-dimensional "flow volume tunnel" (FVT) (See FIGS. 6-8). The length of the tunnel can be modified by changing the time axis, but unlike FVLs that are based on a single breath or average or overlay of three or more breaths, respiratory rate also will be a feature that changes the characteristics of the FVT. The embodiment also generates plots of the FVT image, which can be used by clinicians, physiologists or other users to evaluate the respiratory status, disease state or response to stimulus or therapy. Using customized machine learning software code, these FVL images and secondary calculations and FVT images and secondary calculations preferably become additional parameters that describe the respiratory state of monitored person. This embodiment allows for organization and presentation of FVL and FVT plots, graphics, numerics, and correlation with the database of respiratory states to enhance the users' ability to measure changes in breathing patterns or identify normal/abnormal or healthy/pathological respiratory states.

An embodiment is preferably in the display engine to combine real-time graphical display of volume and flow tracings and absolute values for volume and/or respiratory rate based on tracings. The computer code preferably resides on a processing unit contained in the device used to acquire the respiratory volume trace, enabling the calculation and plotting of instantaneous respiratory volume, respiratory rate and changes in respiratory flow as the data are acquired. The volume information, along with the instantaneous flow rate at the same time, are preferably both plotted on perpendicular axes and results in the flow-volume-loop (FVL), along with the current respiratory status of the patient as indicated by numerical indices. In a preferred embodiment, bioimpedance measurements provide the data for the FVL and FVT and respiratory parameters calculated and these measurements are preferably accurate due to the preferred placement of electrodes on the upper torso of the subject. In this embodiment, together, the process unit, the electrode pads, software, and display combine these streams of information for display to the user. The information displayed includes, but is not limited to, volume, flow, and respiratory status as plotted by tracings or presented by numerics. The data presented informs on the status of, and is not limited to, volume inspired during spontaneous or natural breathing ("tidal volume" or "tidal breathing"), the number of breaths in a given time frame during tidal breathing ("respiratory rate") and the total volume of air inspired in a minute during tidal breathing ("minute ventilation"), and so forth. Tidal breathing values, FVLs, FVTs, and patterns thereof may be determined or documented to change based on an individual's level of exercise, level of metabolism, response to drug or device therapy, therapeutic manipulations, response to specific protocol for action, disease state such as congestive heart failure, sepsis, COPD, cystic fibrosis, bronchopulmonary dysplasia, restrictive pulmonary disease. In one embodiment, computer code preferably is configured to operate on each FVL or FVT by curve fitting and other operations based on custom algorithms, with the insight that different parts of the FVL can be fitted by different algorithms and models.

In one embodiment, the measurement apparatus, the computer processing unit, and the display unit can all reside in physically discrete locations and communicate via local and Internet based communications networks.

In another preferred embodiment of the invention, the system is comprised of a processing unit externally located to the measurement apparatus with its internal processing unit, and uses computer program code written to generate the visual plots and numerical indices for display to users. The external processing unit is preferably connected to the measurement apparatus by wireless (e.g. Bluetooth, Wi-Fi, near-field communications, short-wave radio, cellular data transmission, etc.) or wired ethernet connection. The measurement apparatus preferably transmits impedance and volume information to the external processing unit, which contains the software program required to calculate and display the plots and numerical indices as described in the first embodiment. The invention preferably allows for timely distribution of the measured data to the externally located computer processing unit, which preferably runs computer programs for processing measurements from a single individual or from multiple individuals for display. The display can be located away from the patient and can also display plots and numeric values for more than one patient.

Another embodiment of this invention preferably includes a measurement apparatus that works in the absence of a computer processing unit and can send volume and impedance traces to an externally located computer processing unit, as in the case of other embodiments of the invention. The externally located processing unit can then collect, process, and present the traces, plots, and numeric values at multiple display locations, including display monitors at the measurement source, that is, where the patient rests, and at monitoring locations as specified by the end user.

Another embodiment of this invention is preferably that the measurement apparatus and internal computer processing unit function (as described in the first and second embodiments) to send information to external computer processing and data storage units (together referred to as "servers"). The data is sent by wired or wireless ethernet or other wireless methods (e.g. Bluetooth, Wi-Fi, near-field communication protocols, over cellular networks, etc.), or by transfer of data by storage mechanisms provided by the user. The server collecting the remotely captured measurements can be under physical control of a medical care organization such as a hospital or by a commercial entity or contracted to a third-party vendor that provides remote hosting and computing services (the latter referred to as "cloud-based server"). The physiological dataset can be transmitted to the server, where custom computer executable instructions installed on the server can process the dataset and generate representations of FVL/TBFVL graphical and numerical data for presentation to the user. This server system (controlled directly by the company or contracted through cloud-services vendors) can thus perform computational operations on the volume traces to generate plots, numeric values indicating respiratory status, and traces for display and further analysis. This embodiment preferably allows for processing and storage across multiple patients from a point of care area, care unit within a single location (hospital or hospital systems), and across multiple monitoring locations. The monitoring locations are defined as locations that have a physical instance of the inventions described here, or are obvious extensions of the invention, regardless of whether the location is in a point of care area attended by a health professional, at home, or in non-health care locations such as but not limited to fitness centers, gyms, schools, ball fields, and so forth.

One embodiment of the invention is directed to a method of displaying flow-volume loops of a patient and variability of the flow-volume loops across measured breaths. The method comprises the steps of obtaining a physiological dataset of the patient on a data acquisition device, applying a smoothing and curve fitting algorithm to the physiological dataset on a processing device to obtain real-time volume and flow data at a plurality of time instances, applying a visualization algorithm on the processing device to the volume and flow data to create a series of flow-volume loops based on the volume and flow data, and outputting a plot of the flow-volume loops on a display device to aid evaluation or diagnosis of the patient.

Preferably, the method further comprises pairing flow volume loops with metrics of tidal volume and respiratory rate. Preferably, the method further comprises applying matching algorithms on the processing device to identify normal flow-volume loops and flow-volume loops that indicate likely pathological states or states of altered physiology. Preferably, the method further comprises tracking and updating flow-volume loops on the processing device to identify response to at least one of treatment, change in activity, change in exercise regimen and therapeutic manipulations. Preferably, the method further comprises displaying on the display device at least one indication of the effectiveness of at least one of treatment, change in activity, change in exercise regimen, and therapeutic manipulations.

In a preferred embodiment, the data acquisition device, the processing device and the display device are coupled over a by distance by a communication network. Preferably, the physiological dataset is a respiratory dataset or a cardiac dataset. Preferably, the smoothing and curve fitting algorithms are one of a moving average algorithm, a digital filter algorithm, and fitting via iterative, error reducing learning algorithm. In a preferred embodiment, multiple flow-volume loops are overlaid on the displayed device. Preferably, the overlaid loops are integrated into a representative loop.

Multiple flow-volume loops are preferably graphed adjacently to display differences between the flow-volume loops. Preferably the adjacently graphed flow-volume loops are displayed in a spiral configuration. In a preferred embodiment, a flow-volume loop is segmented into separate components and each component is analyzed individually. Preferably, an automated, unsupervised algorithm identifies flow-volume loops of interest via matching algorithms. Preferably, the method further comprises creating a database wherein diagnostic information related to flow-volume loops are continually updated and classified according to clinically relevant respiratory-system related diagnoses.

Preferably, the method further comprises creating a database wherein diagnostic information related to flow-volume loops are continually updated and classified according to clinically relevant cardiac-system related diagnoses. Preferably, the method further comprises creating a flow-volume template to facilitate algorithmic identification of continuously generated flow-volume loops that match or fall outside the template. Preferably, the flow-volume loops are collected from a nonintubated patient. In a preferred embodiment, the flow-volume loops are collected with an electrical impedance monitor. Preferably, the flow-volume loops are paired with ongoing volume measurements corrected for patient parameters. The flow-volume loops are preferably paired with ongoing respiratory rate evaluation.

In a preferred embodiment, the flow-volume loops are paired with ongoing heart rate evaluation. Preferably, the flow-volume loops are paired with both ongoing volume and ongoing respiratory rate evaluation. Preferably, the flow-volume loops are paired with both ongoing stroke volume and ongoing heart rate evaluation. Preferably, the method further comprises classifying the flow-volume loops for analysis, interpretation and display based on respiratory rate and/or volume measurements. Preferably, the method further comprises interpreting the flow-volume loops for diagnosis, response to changes in physiology, response to interventions based on respiratory rate and/or volume measurements. Preferably, the method further comprises triggering at least one of an alarm, an alert, or an annotation in a record if one or more flow-volume loops are outside of predetermined parameters or if one or more flow-volume loops deviate from previous flow-volume loops by predetermined deviation.

Another embodiment of the invention is directed to a system displaying flow-volume loops of a patient and variability of the flow-volume loops across measured breaths. The system comprises a data acquisition device obtaining a physiological dataset of the patient, a processing device applying a smoothing and curve fitting algorithm to the physiological dataset to obtain real-time volume and flow data at a plurality of time instances, wherein the processing device applies a visualization algorithm to the volume and flow data to create a series of flow-volume loops based on the volume and flow data, and a display device outputting a plot of the flow-volume loops to aid evaluation or diagnosis of the patient.

In a preferred embodiment, the processing device pairs flow volume loops with metrics of tidal volume and respiratory rate. Preferably, the processing device applies matching algorithms to identify normal flow-volume loops and flow-volume loops that indicate likely pathological states or states of altered physiology. Preferably, the processing device tracks and updates flow-volume loops to identify response to at least one of treatment, change in activity, change in exercise regimen and therapeutic manipulations. Preferably, the display device displays at least one indication of the effectiveness of at least one of treatment, change in activity, change in exercise regimen, and therapeutic manipulations. In a preferred embodiment, the data acquisition device, the processing device and the display device are coupled over a by distance by a communication network. Preferably, the physiological dataset is a respiratory dataset or a cardiac dataset Preferably, the smoothing and curve fitting algorithms are one of a moving average algorithm, a digital filter algorithm, and fitting via iterative, error reducing learning algorithm. In a preferred embodiment, multiple flow-volume loops are overlaid on the displayed device. Preferably, the overlaid loops are integrated into a representative loop. Preferably, multiple flow-volume loops are graphed adjacently to display differences between the flow-volume loops. In a preferred embodiment, the adjacently graphed flow-volume loops are displayed in a spiral configuration.

Preferably, a flow-volume loop is segmented into separate components and each component is analyzed in individually. In a preferred embodiment, an automated, unsupervised algorithm identifies flow-volume loops of interest via matching algorithms. The system preferably further comprises a database wherein diagnostic information related to flow-volume loops are continually updated and classified according to clinically relevant respiratory-system related diagnoses. The system preferably further comprises a database wherein diagnostic information related to flow-volume loops are continually updated and classified according to clinically relevant cardiac-system related diagnoses.

Preferably, the processing device creates a flow-volume template to facilitate algorithmic identification of continuously generated flow-volume loops that match or fall outside the template. Preferably, the flow-volume loops are collected from a non-intubated patient. In a preferred embodiment, the data acquisition device is an electrical impedance monitor. Preferably, the flow-volume loops are paired with ongoing volume measurements corrected for patient parameters. Preferably, the flow-volume loops are paired with ongoing respiratory rate evaluation. In a preferred embodiment, the flow-volume loops are paired with ongoing heart rate evaluation.

In a preferred embodiment, the flow-volume loops are paired with both ongoing volume and ongoing respiratory rate evaluation. Preferably, the flow-volume loops are paired with both ongoing stroke volume and ongoing heart rate evaluation. Preferably, the processing device classifies the flow-volume loops for analysis, interpretation and display based on respiratory rate and/or volume measurements. Preferably, the processing device interprets the flow-volume loops for diagnosis, response to changes in physiology, response to interventions based on respiratory rate and/or volume measurements. The system preferably further comprises at least one of an alarm, an alert, or an annotation in a record that is triggered if one or more flow-volume loops are outside of predetermined parameters or if one or more flow-volume loops deviate from previous flow-volume loops by predetermined deviation.

Other embodiments and advantages of the invention are set forth in part in the description, which follows, and in part, may be obvious from this description, or may be learned from the practice of the invention.

DESCRIPTION OF THE DRAWING

The invention is described in greater detail by way of example only and with reference to the attached drawing, in which:

FIGS. 3A-C Flow-volume loops for maximum voluntary ventilation (MVV), heavy exercise, and obstructive disease, respectively.

DESCRIPTION OF THE INVENTION

As embodied and broadly described herein, the disclosures herein provide detailed embodiments of the invention.

However, the disclosed embodiments are merely exemplary of the invention that may be embodied in various and alternative forms. Therefore, there is no intent that specific structural and functional details should be limiting, but rather the intention is that they provide a basis for the claims and a representative basis for teaching one skilled in the art to variously employ the present invention.

Figure 1:
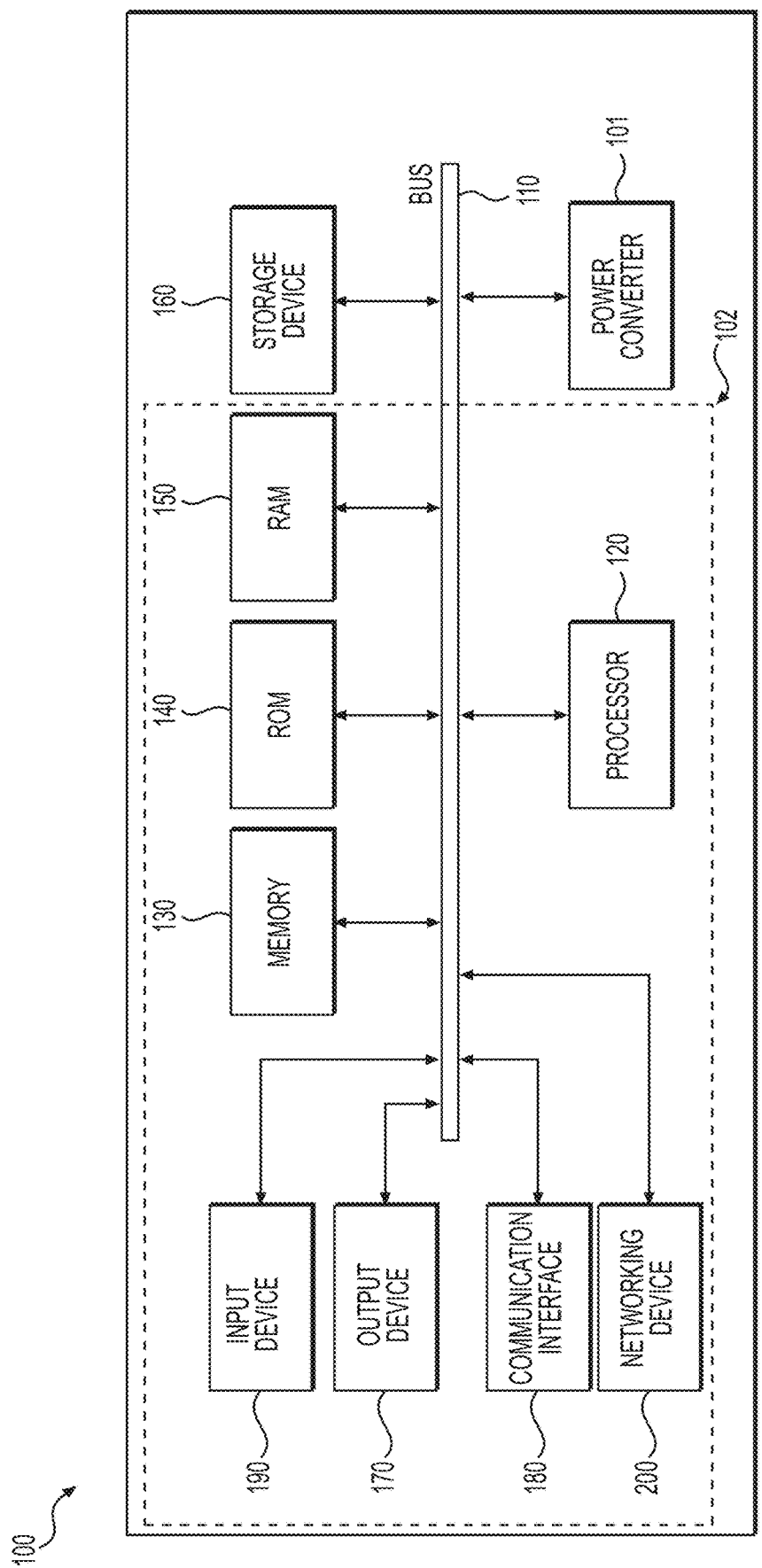
FIG. 1 A schematic of a preferred embodiment of a computing device 100 of the current invention.

FIG. 1 depicts a schematic of a preferred embodiment of a computing device 100 of the current invention. In the preferred embodiment computing device 100 is a streaming media device. Device 100 includes a power converter 101 that may convert from alternating current (AC) to direct current (DC). Preferably, the power converter 101 accepts 120 volts at 60 hertz and may be adapted to another standard international voltage. The outlet connector may be polarized, may include a grounding blade, and may be adapted to domestic or international outlets. Additionally, as described herein, the blades may provide for heat dissipation.

Power converter 101 is used to supply power to the remaining components of streaming media device 100. Streaming media device 100 further includes an integrated circuit (i.e. a system on a chip (SoC)) 102. The SoC integrates multiple components of a computer or other electronic system into a single chip. It may contain digital, analog, mixed-signal, and radio-frequency functions all on a single chip substrate. SoC 102 preferably incorporates a central processing unit (CPU), a graphics processing unit (GPU), and a system bus that couples various system components including the system memory, dynamic random access memory (RAM) 150 and flash memory 130, to the SoC 102. The system bus may be one of several types of bus structures including a memory bus or memory controller, a peripheral bus, or a local bus using one of a variety of bus architectures. A basic input/output (BIOS) stored in flash memory 130 or the like, may provide the basic routine that helps to transfer information between elements within computing device 100, such as during start-up. The drives and the associated computer readable media provide nonvolatile storage of computer readable instructions, data structures, program modules and other data for computing device 100. The basic components are known to those of skill in the art and appropriate variations are contemplated.

Although the exemplary environment described herein employs flash memory, it is appreciated by those skilled in the art that other types of computer readable media which can store data that are accessible by a computer, such as magnetic cassettes, hard drives, digital versatile disks, cartridges, random access memories (RAMs), read only memory (ROM) 140, a cable or wireless signal containing a bit stream and the like, may also be used in the exemplary operating environment.

Computing device 100 further includes a networking device 200. Networking devices 180 and 200 is able to connect to, for example, the Internet, one or more Local Area Networks ("LANs"), one or more Metropolitan Area Networks ("MANs"), one or more Wide Area Networks ("WANs"), one or more Intranets, etc. The networking device 200 can be of an SoC design, with multiple connectivity modules available including Bluetooth and wireless ethernet devices. Preferably, the Bluetooth module may be capable of connecting to wireless Bluetooth devices (e.g. a keyboard or a mouse). Preferably, networking device 200 contains a wireless networking device (e.g. Wi-Fi), however hard-wired networks can be coupled to communication interface 180 (e.g. ethernet and RJ-45). Furthermore, networking device 200 may also connect to distributed computing environments where tasks are performed by local and remote processing devices that are linked (either by hard-wired links, wireless links, or by a combination thereof) through a communications network. In a distributed computing environment, program modules may be located in both local and remote memory storage devices.

Other examples of this system, in addition to the SoC design, include computing device 100 connected to a video display by output device 170, with the video display positioned external to the computing device 100. As another embodiment, the computing device 100 can be designed into an integrated display (e.g. a tablet PC). As another embodiment, the computing device 100 can operate without any video display but can transmit the patient acquired data directly to an externally located computing device via communication interface 180 or networking device 200.

To enable user interaction with computing device 100, there is an input receiving device 190. Input receiving device 190 can receive input from a number of input mechanisms, such as a microphone for speech, a touch-sensitive screen for gesture or graphical input, a keyboard, a mouse, motion input, RJ-45, USB, and so forth. In some instances, multimodal systems enable a user to provide multiple types of input to communicate with the computing device 100. There is no restriction on the invention operating on any particular hardware arrangement and therefore the basic features here may easily be substituted for improved hardware or firmware arrangements as they are developed.

Computing device 100 further includes at least one output port 170. Output port 170 connects computing device 100 to a TV, speaker, projector, or other audio visual device. Preferably, output port 170 is a HDMI port, optical audio port, serial port, USB port, networking port, s-video port, coaxial cable port, composite video, composite audio, and/or VGA port. In preferred embodiments, computing device 100 may also include additional auxiliary components (e.g. power management devices or digital audio convertors).

For clarity of explanation, the illustrative system embodiments are presented as comprising individual functional blocks. The functions these blocks represent may be provided through the use of either shared or dedicated hardware, including, but not limited to, hardware capable of executing software. For example, the functions of one or more processors presented in FIG. 1 (processor 120) may be provided by a single shared processor or multiple processors. (Use of the term "processor" should not be construed to refer exclusively to hardware capable of executing software.) Illustrative embodiments may comprise microprocessor and/or digital signal processor (DSP) hardware, read-only memory (ROM) for storing software performing the operations discussed below, and random access memory (RAM) for storing results. Very large scale integration (VLSI) hardware embodiments, as well as custom VLSI circuitry in combination with a DSP circuit, may also be provided.

Embodiments within the scope of the present invention include computer-readable media for carrying or having computer-executable instructions or data structures stored thereon via storage device 160. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Most importantly, these aspects of computer-executable instructions are modular and can be run in a single computer device, across multiple computer devices connected by input device 190 and output device 170, or across computer devices that are connected by communication interface 180 and or networking device 200. The computer-executable instructions can be adapted to work on concurrently on multiple devices with the data shared among them or remotely and at different times by means of data transmission and storage. These can be thought of as additional exemplars of a local and integrated device and network-based computing device to calculate and displaying continuously monitored tidal breathing flow-volume loops, at a destination of the users' choosing. The hardware and software modules can be embodied in one device, or arrayed across devices separated by distance, but connected by means of a communication network.

The preferred embodiment of the invention is a device and method for collecting and displaying a respiratory volume trace, obtained by a non-invasive respiratory volume monitor, in graphical form in which instantaneous respiratory volume (V) is plotted along one axis and changes in respiratory flow (i.e. the change of respiratory volume as a function of time, dV/dt) is plotted along a second axis. From this type of representation, more complex mathematical descriptors can be generated. The FVL can be separated into sub-components (for example, by identifying peaks by the first derivative of the flow or by inflection points as determined by the second derivative of the flow or by other functions) and be analyzed using different mathematical functions to fit the curve segments, including but not limited to hyperbolic and parabolic functions, linear regression, polynomial fit and wavelet analysis. The coefficients that describe how well the functions fit the data, and the equation parameters generated become additional ways of describing the FVLs mathematically. These numerical values can be combined with other respiratory parameters to act as indices for comparing to canonical, typical FVLs derived from specific populations. While the invention is described with respect to respiration, the system and methods may be adapted for flow volume loop for cardiac purposes with blood flow using stroke volume and cardiac output or cardiac index. Furthermore, the system can use pressure volume loops for respiration.

In one embodiment the respiratory volume monitor is preferably an impedance-based Respiratory Volume Monitor (RVM). In one embodiment, the respiratory volume (V) is preferably plotted along the x-axis and the flow (dV/dt) along the y-axis of a conventional Cartesian coordinate system. In another embodiment, the two variables are preferably plotted along the r and Theta axis of a polar coordinate system. These plots can be displayed as the data are captured by the RVM device, showing the construction of each flow-volume loop to the user in a circular "radar-sweep" like animation. The embodiment can also be configured to display only the finished flow-volume loop plot.

In one embodiment the instantaneous flow (y axis)/time (x axis) tracing is preferably displayed to show changes in waveform morphology that may indicate inspiratory and/or expiratory airflow abnormalities otherwise only available with a calibrated spirometer. In another embodiment, the shape of the flow time waveform is characterized by measurements of the slope of the inspiratory and/or expiratory phase as an indicator of flow abnormalities and attendant changes associated with intervention. In each embodiment, graphical or numerical, these patient specific measurements may be compared to those derived from a large but representative population, or from a baseline standard from the same patient but identified by the clinical end-user.

In one embodiment, flow-volume loops are preferably normalized and presented as a percent of the patient's predicted values (as % Pred or % of Pred) for both flow and volume. In one embodiment, these predicted values are preferably derived from a large population of representative subjects. In another embodiment, these predicted values can be derived from each individual patient during a "baseline" respiratory state: for example, in an asthmatic patient, the "baseline" volume and flow may be calculated during period of normal breathing without an asthma attack, so that values obtained during an asthma attack can then be normalized by these "baseline" values. These values can be calculated following administration of an inhaled pharmaceutical, oral pharmaceutical, intravenous pharmaceutical or delivery of other therapy. Other disease states may include restrictive disease, retained secretions, atelectasis, pneumonia, cardiac failure, congestive heart failure and other forms of obstructive or restrictive disease. Other therapies that may be administered and therapeutic efficacy evaluated may include airway recruitment maneuvers, suctioning, percussion, vibration, vest-based vibration, intermittent positive pressure breathing (IPPB), different air delivery strategies or patterns for patients on a ventilator. In another embodiment, these predicted values may be normalized to anthropomorphic variable such as age, height, weight, and gender, or physiologic variables such as heart rate or blood pressure, measurements of diaphragmatic excursion, blood carbon dioxide levels, end tidal carbon dioxide, transcutaneous carbon dioxide, blood oxygen levels or oxygen saturation. In another embodiment, many data streams from multiple patients can be sent by communications module to a programmable element to continually sample and derive new average respiratory states by identifying and incorporating additional data from new but still representative subjects. In this embodiment, the servers can be under direct physical control or contracted to a third-party provider of processing and storage services (i.e. "cloud-based computing").

In a preferred embodiment these flow volume loop images are paired with specific respiratory rate and/or respiratory volume measurements to provide a more advanced assessment of respiratory status. The meaning of the shape of the FVL is different with different respiratory volumes such as tidal volume, functional residual capacity, total lung capacity, forced vital capacity, forced expiratory volume, forced expiratory flow 25-75%, peak expiratory flow, maximum voluntary ventilation, slow vital capacity, residual volume, expiratory reserve volume and other metrics used in pulmonary function testing and exercise physiology, like VO2, VCO2, PetCO2, RER, SaO2 or any combination, ratio, or product of these metrics. Each of the volume metrics can be put into the context of predicted volumes for a given patient based on parameters including height, weight, gender, age, race, etc or compared with baseline measurements collected either at rest or after a specific respiratory maneuver, treatment, change in activity or exercise program, or therapeutic manipulation. Pairing the FVL shape with other respiratory metrics preferably puts the shape of the curve in context with expected changes at larger volumes for a given individual that may not be apparent at lower volumes. This pairing of the FVL with respiratory metrics is preferably used for respiratory status, respiratory performance, alterations in respiration from medication or other therapy, response to specific respiratory stimuli, monitoring of respiration over time during daily life or during specifically designated activities, diagnosis of disease and monitoring of therapeutics and therapeutic manipulation. Additionally, including respiratory rate into the analysis of the FVL preferably provides additional information for respiratory assessment, diagnosis and monitoring of therapeutics. The FVL can be paired (either based on absolute values or corrected for patient specific parameters) with any of the following: volume metrics, respiratory rate, response to therapeutics.

Figure 7A:
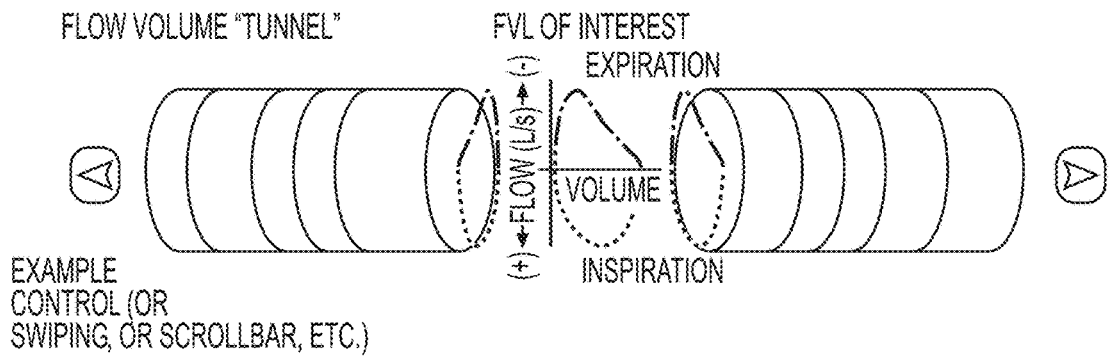
FIG. 7A A representation of FVL's, arranged in flow tunnel with the current FVL (and associated parameters) displayed on screen.
Figure 7B:
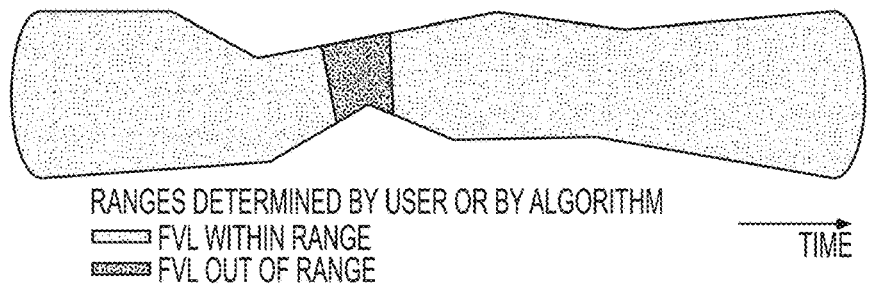
FIG. 7B Flow volume tunnel represented in schematic form, with the yellow segment highlighting when FVL's were out of range.
Figure 7B:
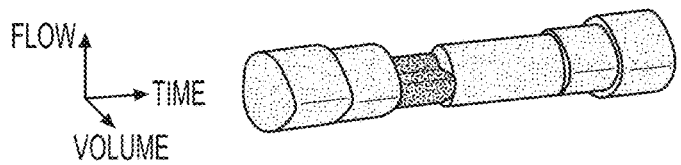

In one embodiment, a separate flow-volume loop is preferably generated for each breath (from beginning of inspiration to end of expiration). New flow-volume loops are preferably plotted after the old ones are erased from the screen. In another embodiment, flow volume loops of individual breaths are preferably plotted over the loops from prior breaths with the starting point (e.g., x-y coordinates, aligned across breaths). In one embodiment, the loops of the prior breaths preferably fade as a function of time, such that at any point in time there are a maximum number (e.g. 5, 10, or 50) visible as defined by manufacturer defaults or by the end-user. In another embodiment, individual breath flow-volume loops are preferably offset along one of the axes (for example, the x-axis) corresponding to their temporal sequence: for example, each breath's loop may be plotted 1 mm to the right of the previous breath's loop, creating a "flow-volume tunnel" (See FIGS. 7A and 7B). The user can select the flow-volume loop of interest by scrolling through the tunnel by swiping through the tunnel, dragging, or pressing directional icons on screen. As the new flow-volume loops come into focus, they may rotate to present to the user in traditional 2-dimensional, Cartesian coordinate system and then rotate back and flatten into the tunnel stack as users move away from them (See FIG. 7A). Below these flow-volume tunnel and the individual flow-volume loops different numerical values calculated from these data are preferably presented. These numerical values and indices, not all of which need to be presented to the user at the same time, may be used for automated classifier schemes or indicate the groupings to which the flow-volume loop has been classified. For example, respiratory status can be represented by arrays, or sets, of measured values; in other cases, custom software can generate indices, which represent the categories determined by the classifier program. These can also be stored and be readied for viewing to facilitate comparisons between user interpretations and machine calculated sorting algorithms.

Figure 7C:
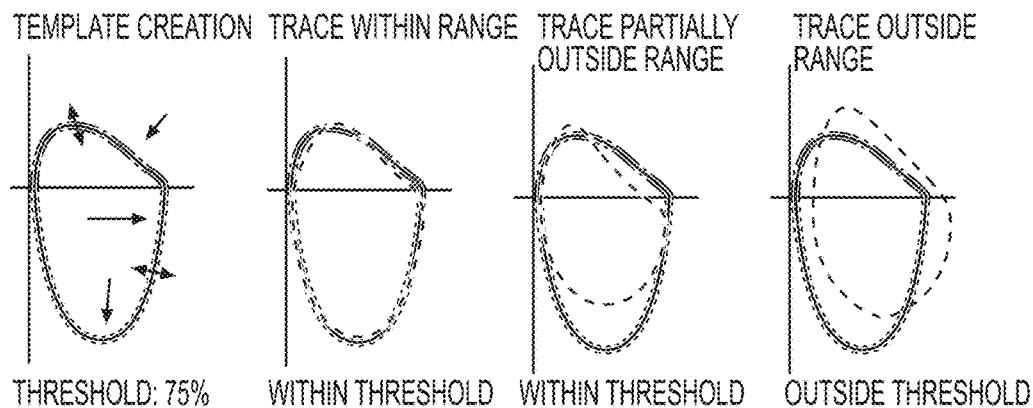
FIG. 7C A template can be created to help triage/sort actual FVLs for each breath.
Figure 8A:
FIGS. 8A-C (A) Detailed examples of FVL's and how they can be arranged to form a FVL "tunnel." In this representation, changes in respiratory rate are depicted as changes in the density (decrease or increase in the temporal spacing) between consecutive FVLs (B) whereas changes in volume are depicted as changes in the shape and size of the FVLs (C). (D) Depiction of FVL tunnels corresponding to various respiratory states.
Figure 8B:
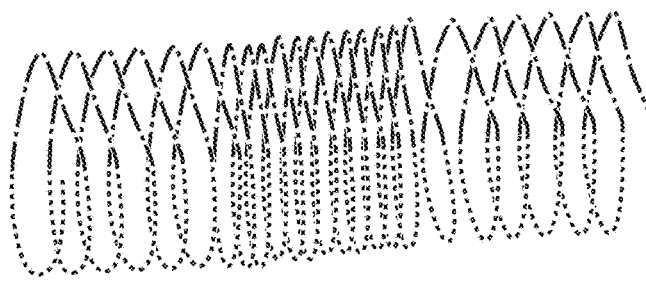
Figure 8C:
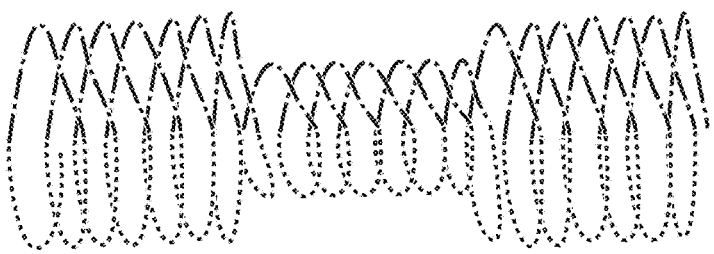
Figure 8D:
Figure 8D:
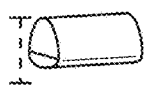
Figure 8D:
Figure 8D:

In one embodiment, the flow-volume loop as plotted on a Cartesian coordinate system can be treated as a 2-dimensional image, to compare the individual breath against a canonical representations of flow-volume loops for a given respiratory state of interest (such as activity induced changes in respiration, disease progression, pathological states, pharmaceutical agent response, and so forth) (See FIG. 7C). The comparison can easily be extended to multiple traces by drawing them on top of one another, creating an average representation of the breaths. This image comparison is preferably performed by the creation of correlation maps that score how much overlap there is between any two images of flow-volume loops; multiple comparisons can be made by calculating the correlation coefficients in all pairwise groupings possible. The flow-volume loops are preferably first normalized to maximum volume displacement and maximum absolute flow magnitude, where maximal flow can be observed during either expiration or inspiration. These normalized traces are preferably shapes that can be compared as images, as they preferably have the same image-dimensions. Noise reduction and sensitivity can be further controlled by image smoothing by convolution with differently sized and constructed kernels. Preferably the more overlap there are between these traces as images, the higher the correlation coefficient and thus more similar in shape the two are. In this embodiment, preferably any two flow-volume loops can be compared, whether they are individual breaths of interest, or the derived representation from a particular respiratory state, or some form of averaged FVL representation.

In one embodiment, each flow-volume loop generated from data streamed from the RVM can be explicitly compared to a set of breaths (a "table" or "library") stored on the preferred computing device 100, in the memory device(s) 130, 140, and 160. The set of breaths stored on the device may be averaged representations of the FVLs and their associated numerical parameters, or multiple individual FVLs and their parameters, from representative groups for different respiratory states. By comparing the recorded FVL and parameters from stored FVL and parameters, a similarity index to the various respiratory states can be generated for every recorded breath.

In one embodiment, patient FVLs and parameters can be compared to FVLs and parameters generated from the same patient during "baseline" recordings as determined by the user. This embodiment allows for explicit monitoring for respiratory state changes states that change due to activity or exertion, treatment progression, disease progression, pathological states, pharmaceutical agent response, and so forth. These state changes can be tracked by numerical parameters or by graphical analysis of the FVL.

In one embodiment, the single FVL can be compared to all FVLs in a previously collected dataset (a "library"). The preferred device (e.g. some variant of computing device 100) can transmit data to servers and measured respiratory and patient data be compared to the "library" of breaths stored. The computer-executable instructions can be modified to run on the server and perform the same operations on the respiratory data as described herein. This embodiment preferably accounts for the expanding set of data measured by many instances of the current invention at multiple locations and will incorporate these into the "library" containing breaths organized into respiratory states, both normal and abnormal. This embodiment will preferably enable the user to display the results, including but not limited to indices, FVLs, tracings, and parameters at a location of their choosing, for review. This embodiment preferably indicates that the number of comparisons can increase as the library continues to expand as new, validated data are added to servers. This embodiment will preferably also enable comparisons of many different streams of data being transmitted to the server and for display to the user, with the data streams being sourced from medical and non-medical care facilities, including but not limited to, home sites, fitness centers, clinics, mobile clinics, hospitals, schools, and so forth.

In one embodiment, the library of FVLs may be continually analyzed and correlated with presentation of symptoms and patient demographics as recorded in electronic medical records. To facilitate this work, RVM data will preferably be transmitted to servers along with non-RVM data provided by consenting parties. Computer instruction will preferably be modified to generate indices describing the FVLs and correlating them with patient or other user derived information to create probability maps, that is predictive measures, of likelihood of abnormal respiratory states, where a current diagnosis is missing. This predictive measure can also reaffirm positive diagnoses or effects of therapeutics.

In one embodiment, users may have the ability to set their own limits and use the RVM to trigger an alert when the limits are surpassed (or fail to be reached). In one embodiment, the numerical parameters can be used as thresholds, and users can enter their own parameter limits and determine whether the FVL and tracings need to remain under or surpass the limit to trigger the alert. In one embodiment, the user can manipulate a template FVL by means of a touch-screen interface, drawing the idealized FVL as in FIG. 7C. The user can specify the area around the FVL to set the range of values they accept by thickening the line specifying the FVL, with the RVM alerting whenever FVLs from individual breaths fall out of range of the drawn FVL template. These limits may define respiratory states for which the user requires an alert.

In the context of exercise performance, the consolidated data from FVL and respiratory metrics can provide information to modify programs or routines. These data can be simplified for presentation as a single number.

In one embodiment the device can provide an alarm or alert or an annotation in the record provided to the individual or to caregivers or others remotely if an FVL or defined series of FVL with or without associated respiratory metrics are outside of previously selected parameters or if an FVL or series of FVLs with or without associated respiratory metrics deviates from previous FVLs by an amount previously defined. The alarm or alert may remain until addressed or may cease upon return to acceptable parameters.

In one embodiment, FVLs of interest may be identified and stored in memory for review, for example the user may specify that all breaths with tidal volumes larger than 0.8 liters, or smaller than 0.3 liters, and so forth, be marked in some way. Some examples of the visualization may include, but are not limited to, individual FVLs overlaid, an average FVL is displayed, or the flow-volume tunnel is colored to show when the breaths occurred (See FIG. 7C). In this way, the user can assess the frequency of occurrence, when they occurred, and place their occurrence in the context of treatment.

In one embodiment, the FVL can be used in assessment of obstructive sleep apnea and central apnea or neuromuscular diseases such as amyotrophic lateral sclerosis or generalized weakness from long periods of ventilation. For example, for apneic patients one embodiment would provide information combining respiratory rate or apneic pauses with the FVL characteristics of the recovery breaths. For patients with the characteristics of weakened musculature one embodiment would provide data regarding the decrease in flow associated with weak musculature and help define improvement or deterioration. This can assist in defining important features of disease such as flow parameters that define the adequacy of respiratory musculature to overcome obstruction or the speed with which debilitated musculature can provide adequate respiration.

Figure 2:
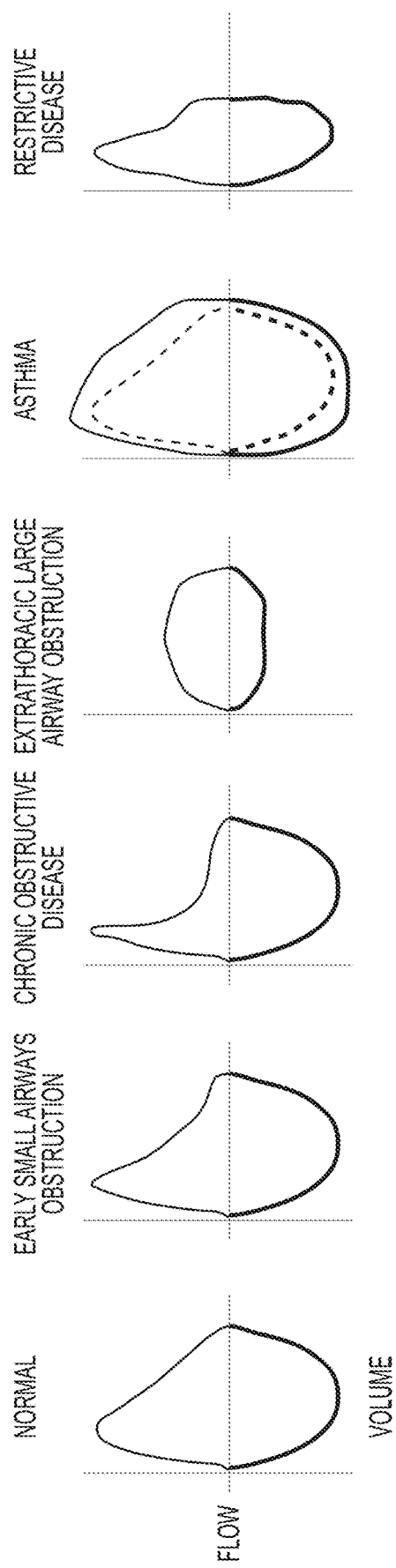
FIG. 2 Representative flow-volume loops for normal and diseased individuals.

In one embodiment, flow-volume loops can be used in the assessment, diagnosis, response to therapeutics and/or prediction of disease state, respiratory status, and/or other clinical conditions. In one embodiment, the shape of a flow-volume loop can be used to aid in the diagnosis or in assessment of a condition (e.g. asthma, COPD, CHF, cystic fibrosis, inflammatory disease states, etc.) (See FIG. 2). In another embodiment the area(s) or shapes(s) or slopes(s) within the inhalation or exhalation portion of the flow-volume loop can be used to aid diagnosis or monitoring of therapeutics or combined with other metrics as described above. In another embodiment, the sum, difference, product, ratio (or a combination of those) between inhalation or exhalation features (area, slope, time, etc.) can be used to aid diagnosis or monitoring thresholds. Similar to a previous embodiment, the graphical and numerical representations derived from a larger, representative population can be selected and displayed to form comparisons.

In each embodiment, the graphical and numerical representations of the flow-volume loop and tunnel can be compared to values and traces derived from a large, representative population with that indication. The specific representation can be tailored for each disease to facilitate diagnosis and assessment. The descriptions herein describe preferred embodiments for using RVM to diagnose and assess normal and abnormal respiratory states, but do not limit additional employments by one skilled in the art. Use of these techniques of FVL and respiratory metric integration, analysis and display can be used with technology providing tidal FVLs such as spirometers, ventilators and pneumotachometers. While tidal FVLs are displayed on ventilators, the tunnel presentation, threshold limits, trending and other features of this invention are surprisingly not currently available.

In one embodiment, the flow volume loops and associated parameters are preferably captured during mechanical ventilation, during extubation, and following extubation to characterize changes in restriction and obstruction to distinctly characterize the patient's ability to breathe spontaneously without mechanical ventilatory support.

In one embodiment, monitoring the flow-volume loops and associated parameters sequentially (whether in complete overlap or in a "tunnel" form) can be used to monitor real time changes in respiratory performance. These changes may be induced by activity level, physical therapy, rehabilitation programs, pre-operative preparation programs or disease progression.

In one embodiment, the shape of flow-volume loops and associated parameters can be used in the assessment of opioid sensitivity, opioid-induced respiratory depression, and/or opioid-induced respiratory compromise. In another embodiment, changes in the shape of flow-volume loops and associated parameters can be used to quantify level of sedation (or opioid use), rate of opioid metabolism, and/or need for opioid reversal treatment (e.g. naloxone).

In another embodiment, the shape of the flow-volume loops and associated parameters can be used in the assessment of the effects of benzodiazepines. In another embodiment, changes in the shape of flow-volume loops can be used to quantify the sensitivity of a patient to pharmaceutical agents, especially those with known or suspected effects on the central and peripheral nervous system.

In another embodiment, the shape of the flow-volume loops and associated parameters can be used in the assessment of the effects of pharmaceuticals used in respiratory diseases such as beta-agonists, steroids, theophylline, aminophylline, acetylcysteine, doxapram hydrochloride In one embodiment, the changes in respiratory performance can be used to assess disease progression (for example in asthma, COPD, CHF, cystic fibrosis, etc.). In another embodiment, the changes in respiratory performance can be used to evaluate the effectiveness of therapy (CPAP, BiPAP, hi flow O2, bronchodilator, etc.). In another embodiment, the changes in respiratory performance can be used to assess the reaction to a broncho-constrictive agent such as cold air, methacholine, or other industrial irritants present in the workplace.

In one embodiment, monitoring flow volume loops during polysomnography and associating them with sleep stages (stage 1-4, REM) or sleep states (wake, non-REM sleep, REM) can be used to detect changes in airflow associated with changes in upper airway resistance (UARS, Upper Airway Resistance Syndrome). In one embodiment, flow volume loop shape and associated parameters changes preceding an apneic or hypopneic event is preferably prognosticative of the severity of the breathing cessation. In one embodiment, loop changes following uvulopalatopharyngoplasty (UPPP) preferably characterize and document the increase in airway patency post-procedure.

In one embodiment, the tidal breathing flow volume loops are preferably characterized by measuring and trending the peak expiratory and peak inspiratory flow at 50% exhaled and inhaled volume. The optimum ratio of 1.0 preferably indicates normal, unobstructed breaths. When the ratio falls below 1.0, it may indicate subtle changes in expiratory flow limitation.

In one embodiment, the tidal volume loop and associated parameters during cardiopulmonary exercise testing, either maximally or submaximally, can be used to determine a ventilatory limitation of the lung. Changes in flow volume loops in conjunction with exercise fatigue preferably determine respiratory limitations and possibly assist in ruling out muscular or cardiac limitations contributing to exercise intolerance. Detection of concavity in the expiratory limb of spontaneous exercise flow volume loops may help assess dynamic hyperinflation and exercise limitation in patients with COPD and other respiratory diseases. In one embodiment, collection of FVL by RVM preferably obviates the requirement for inconvenient and potentially inaccurate collection of data during exercise since no mouthpiece or mask is required. Data can be collected outside of the exercise physiology laboratory in general circumstance of the exercise such as running or bicycling outside, which is a more natural environment and more reflective of the actual training requirements.

In one embodiment, real time flow volume loops and associated parameters collected in a controlled exercise setting for pulmonary rehabilitation can provide information to adequately prescribe an exercise prescription so the patient can perform an exercise program gaining positive benefits without over exerting and inducing unwarranted fatigue, dyspnea, and desaturations. For cardiac and other rehabilitation, collection of data with a mask or spirometer in daily practice is difficult and not practiced. Use of RVM and FVL analysis preferably permits the daily observation of progress in exercise tolerance while providing safety thresholds for ventilation and metabolic effort. One embodiment preferably provides presentation of data with the FVL tunnels and data integration and presentation with data gathered by spirometry or pneumotachometry in the cardiopulmonary laboratory.

In one embodiment, tidal flow volume loops and associated parameters are preferably collected at rest. In a preferred embodiment, the flow volume loops are preferably recorded during normal activities throughout the course of the day, similar to a Holter monitor to assess the variability in respiratory function. This may include the correlation of respiration parameters with journal entries. These data may be used for assessing ongoing disease such as COPD or CHF, assessing the response to therapy for cardiopulmonary disease, assessing the adherence to a therapeutic regimen or for determining the suitability for surgery in general or suitability for pulmonary resection. FVL and pulmonary data can be combined with standard cardiac Holter monitoring for a comprehensive evaluation of the cardiopulmonary system. In another embodiment, the minimum adequate respiratory function is preferably determined for pulmonary resection based on ventilation status and daily requirements in the patients usual setting.

In a preferred embodiment, tests similar to those which are unable to be performed during standard (as determined by the ATS), advanced, and other tests conducted during pulmonary function testing are preferably performed for individuals who cannot effectively cooperate with the standard spirometry testing which requires holding the spirometer in the mouth and simultaneously breathing in deeply and exhaling sharply. This is often challenging or impossible in many elderly, pediatric, or infant patients. The system preferably also provides information that is not altered by the presence of a spirometer mouthpiece in the mouth or mask on the face.

Long term, continuous use of flow-volume measurements has never been possible with spirometer based systems because of the requirement for a mask or mouthpiece and the requirement of a sealed patient breathing "circuit", that is, there are no leaks at any point from the patient's lung, to his/her mouth or nose, with the mouthpiece or mask, and to the spirometer. The users are required to assess continually for leaks or actively maintaining an airtight seal, preventing these measurements on patients who cannot comply. The use of these spirometers are limited to short monitoring periods of a few breaths or a few minutes. With RVM measurements, the physiologic changes that can be visualized with flow volume loops can be associated with physiological or mental stress during a 24-hour, multi-day, 1 week period, or 1 month period or in perpetuity.

Other features of the invention may include, but are not limited to: the respiratory equivalent of Holter monitoring of activities of daily living, changes of certain percentages triggering an alarm, important during awake periods, monitoring during periods of physical or emotional stress, monitoring combined characteristics of sleep and wakeful periods as well as differences between the two, color FVLs under 40% predicted red, orange or dark yellow, color FVLs 40-80 bright yellow and alarm, color FVLs over 300 red orange or dark yellow and alarm, adjust coloring parameters up or down in different, color inspiration green and expiration pink or purple or other colors, color curves more than 50% different from normal predicted and alarm, color curves more than 50% different from patient's usual or baseline curve and alarm, retroactively color curves that are 1SD outliers, color in area between a given curve and predicted curve and alarm if more than x different, color in area between given curve and baseline curve and alarm if x percent different, color area between average of x curves before and x curves after a therapy such as albuterol, calculate percent change in MV and report, determine if change brings above 40% MV predicted and alarm if does not (or 80%), Circadian rhythm, over time, etc., variability, variation, complexity analysis, etc.

The embodiments of the invention described herein facilitate the eventual need to classify additional respiratory states in many more patients, for longer periods of times, all of whom are experiencing respiratory distress in some way.

Figure 3C:
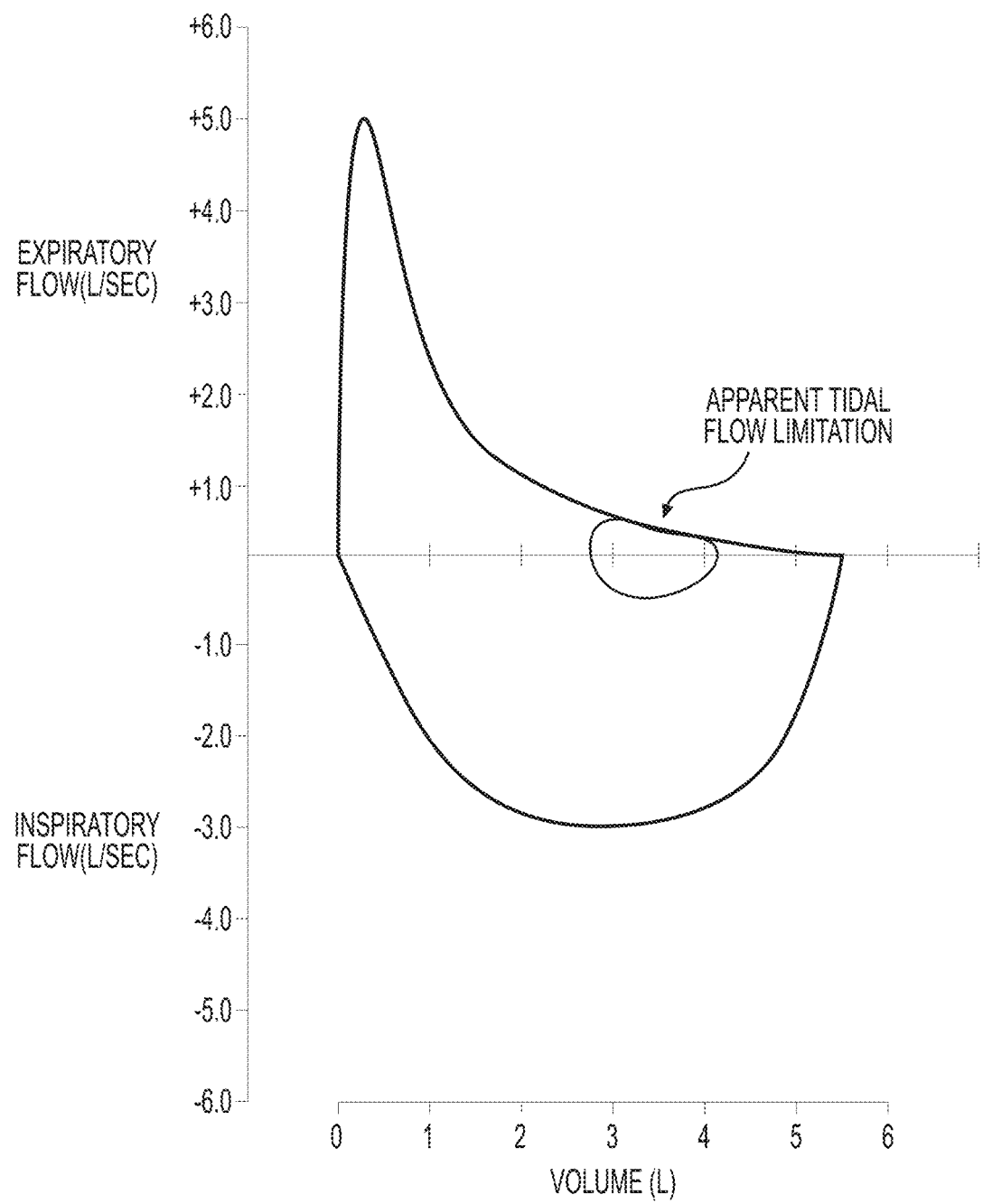

Preferably, the significance of the flow-volume loop is: (1) Provides diagnosis and differential diagnosis for the situation shown in FIG. 2; (2) Provides a new concept of exercise tidal flow volume loop and its clinical significance. The following information can be obtained: (1) the degree of expiratory flow limitation; (2) the maximal expiratory/inspiratory flows available over the range of the tidal breath, (3). Inspiratory flow capacity. See FIGS. 3A-B.

In TBFVL, inspiratory flow limitation is common in sleep related breathing disorders. In TBFVL, expiratory flow limitation is common in reactive airway such as asthma. In TBFVL, the middle portion is more sensitive to sleep apnea-hypopnea syndrome and changes to the middle of the loop is likely an earlier indication of this syndrome. In prehabitation (patient with respiratory disease) and rehabilitation (all patients with abdominal and thoracic surgery, or old patient at risk for pulmonary complications)

The maximal volume of air that can move into or out of a person's lungs is called the Vital Capacity (VC). VC is often measured as a static lung volume to reveal obstructive vs restrictive lung pathology. When the vital capacity is forcefully exhaled, the breathing maneuver is referred to as the Forced Vital Capacity (FVC).

When the FVC volume/time tracing is analyzed, the maneuver reveals airflow limitations into and out of the lung. When the maneuver is traced with the x axis=volume, and the y axis=flow, the pulmonary function maneuver is called the flow volume loop because it presents in the form of a loop that is pathognomonic of a variety of pulmonary disorders/diseases.

The flow variable is preferably derived from the volume/time tracing. If the flow variable is displayed as a function of time, it preferably reveals patterns of flow limitation that are not as easily revealed by the volume/time tracing.

A loop can also be created during spontaneous ventilation (tidal breathing). These so-called tidal volume flow volume loops may also reveal changes in pulmonary function. In particular, monitoring the loops sequentially (overlap) can be helpful to monitor real time changes in breathing, either secondary to disease progression, responsiveness to therapy, reaction to a broncho-constrictive agent such as cold air, methacholine, or other industrial irritants that present in the workplace.

During the FVC maneuver, there are many parameters that can be used to characterize the shape of the loop, and most of these parameters are presented as a percent of the patient's predicted values (% Pred). The predicted values are derived from large populations of normal subjects. By presenting the data as % Pred, the values are normalized to anthropomorphic variable such as age, height, weight, and gender.

The tidal volume flow volume loop is typically analyzed more by changes in shape instead of by comparing to a nonexistent large database of flow parameters during tidal breathing. As such, defining simple parameters such as UAC, inspiratory and expiratory slope of peak-zero flow.

If the system can calculate the first derivate of volume, flow, it can be displayed as flow/time. While the flow/time tracing is useful to determine subtle changes in the airways response, if it can be represented as the y axis of the TV FV loop, it can afford the system the ability to uniquely display the graphic based on a single measurement, Minute Ventilation (MV), the fundamental unit of ventilation.

Using an RVM signal, the loops are preferably created differently than other technologies used in non-intubated patients, respiratory inductance plethysmography, or RIP. The RIP signal is based on the movement of two compartments, the thorax and the abdomen, each contributing a degree of freedom into an error analysis. The invention preferably uses a single parameter that has been verified to be accurate within 10% of a volume/flow calibrated spirometer (flowmeter, heated pneumotach, volume spirometer).

In one embodiment, it has been noted that the morphology of the respiratory volume/time tracing of a spontaneously breathing patient changes following opioid administration. Effectively, the shape suggests that the individual 'forgets to exhale" with a plateau in the volume/time trace. As such, a rendition of the TV/FV loop for these subjects has a unique morphology and can define the impact of opioids on respiratory status, diagnose opioid induced respiratory depression, differentiate opioid induced respiratory depression from other states causing respiratory depression and demonstrate response to opioid reversal agents or the effects of stimulation on respiratory status Capturing FV loops outside of the hospital environment that have this unique morphology may be useful to determine if a subject has drugs in their system, allowing clinical decisions to be made about compliance with detox programs, 30, 60, 90-day readmissions, etc. Preferably, the RVM provides information for FVL/respiratory analysis as a ventilation monitor with the capability of noninvasively and continuously monitoring for inspiratory and expiratory flow and volume using impedance technology which requires no cooperation, can be implemented over long periods of time and is convenient for patients. Traditional methods for gathering flow volume loop data have been dependent on using a mouthpiece and pneumotachometer and patient effort for the conscious patient. Respiratory induction plethysmography (RIP) technology measures changes in rib cage movement using two chest belts.

EXAMPLE

Pulmonary function tests utilize flow-volume loops (FVLs) to help detect, diagnose, and monitor the long-term progression lung disorders such as COPD and asthma. Spirometry is the gold standard for generating FVLs via a forced vital capacity (FVC) test, which measures the amount of air a subject can forcefully exhale. This test requires the patient to be awake, alert, and cooperative which is not always possible, especially for pediatric or geriatric patients. In addition, tidal breathing FVLs have been used to analyze respiratory function under baseline conditions and monitor real time changes in breathing using respiratory inductance plethismography (RIP) bands. Monitoring tidal breathing FVLs is a way of of monitoring disease progression, responsiveness to therapy, reaction to broncho-constrictive agents, and changes in breathing during exercise, but has not been widely adopted due to technology limitations. A non-invasive respiratory volume monitor (RVM) may be used in measuring continuous tidal FVLs in healthy volunteers breathing at a variety of breathing rates in lieu of RIP bands or a spirometer.

Continuous respiratory data including volume traces were collected using an RVM from volunteer subjects. Each subject performed 6 breathing trials at 3 different prescribed respiratory rates. In trials 1 and 6, subjects were instructed to breathe normally. In the middle four trials, the subject alternated between fast (25 bpm) and slow (5 bpm) breathing as set by a metronome. Flow traces were generated by taking the first derivative of the volume traces. To reduce breath-to-breath variability, individual breaths were aligned at the start of inhalation with volume and flow set to "zero". For each breathing trial, breaths were divided into equal time segments and averaged across all breaths within each trial to generate an average "representative" FVL. The system assessed the characteristics of the shape of FVLs for different breathing trials.

Figure 4:
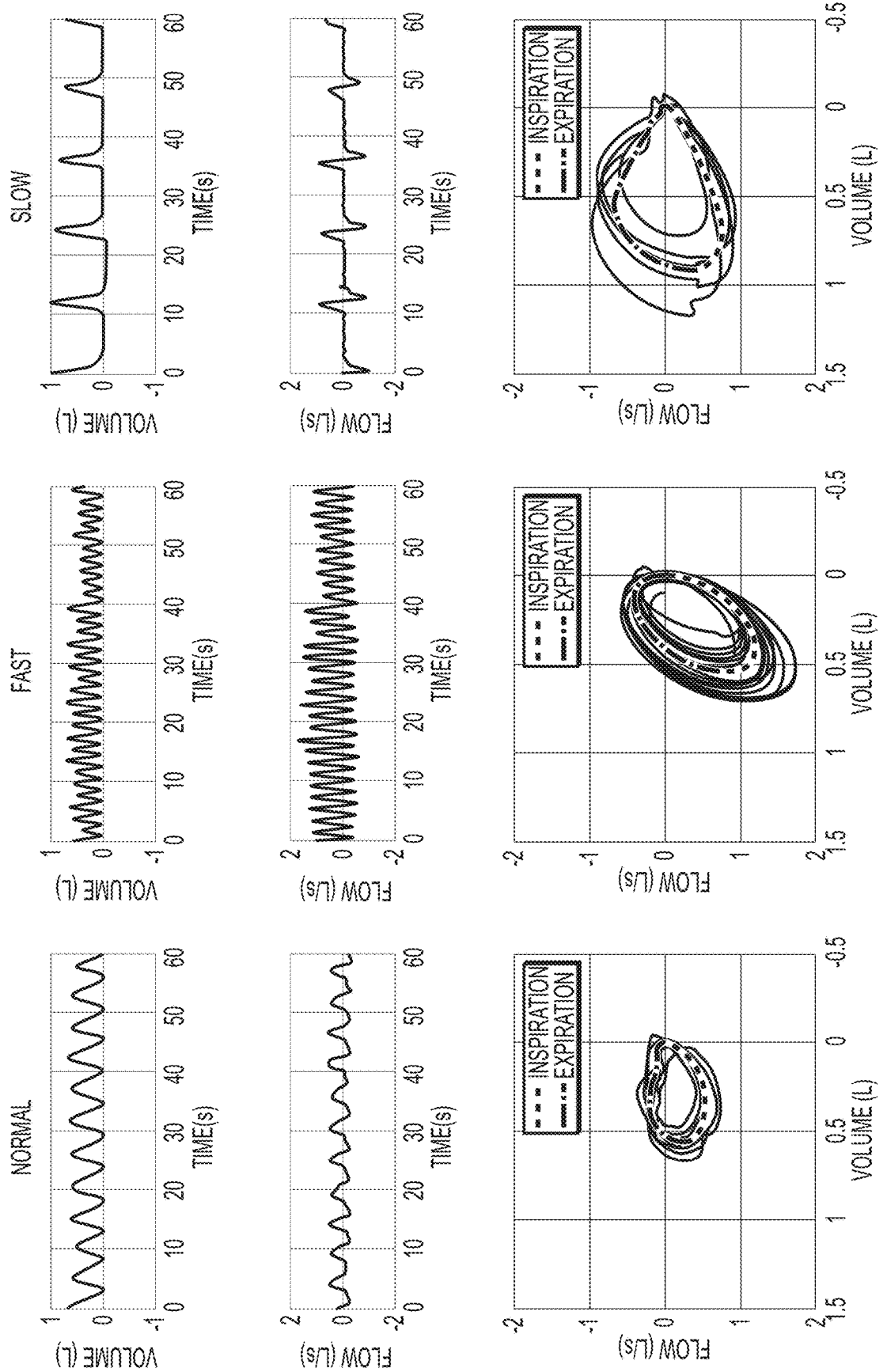
FIG. 4 Representative volume (top row), flow (middle row), and flow-volume loops (bottom row) for normal (left column), fast (middle column), and slow (right column) breathing trials. The flow-volume loops display all breaths during the breathing trials as well as the average inspiratory (dashed) and expiratory (dash-dot) curves. Note that both axes are reversed in accordance with common presentation of flow-volume loops.
Figure 5:
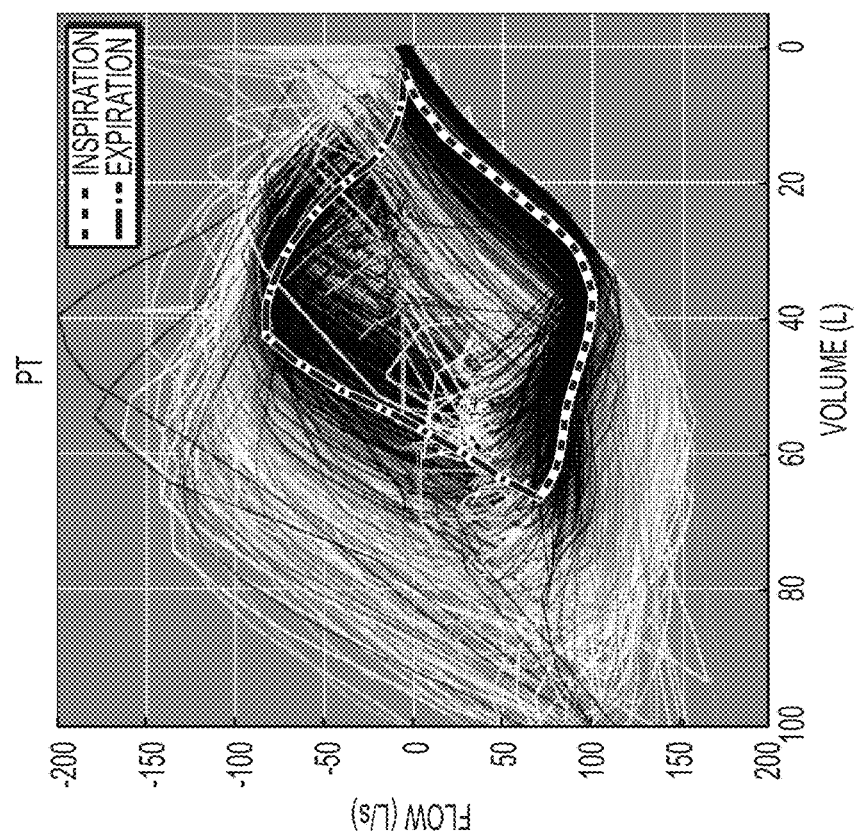
FIG. 5 Representative FVLs from neonatal patients from RVM (left) and a pneumotachometer (right). The visualization of FVLs depicted here can be applied to data from RVM, pneumotachometer, spirometer, ventilator, CPAP, or any other device capable of measuring respiratory flow and volume.
Figure 5:
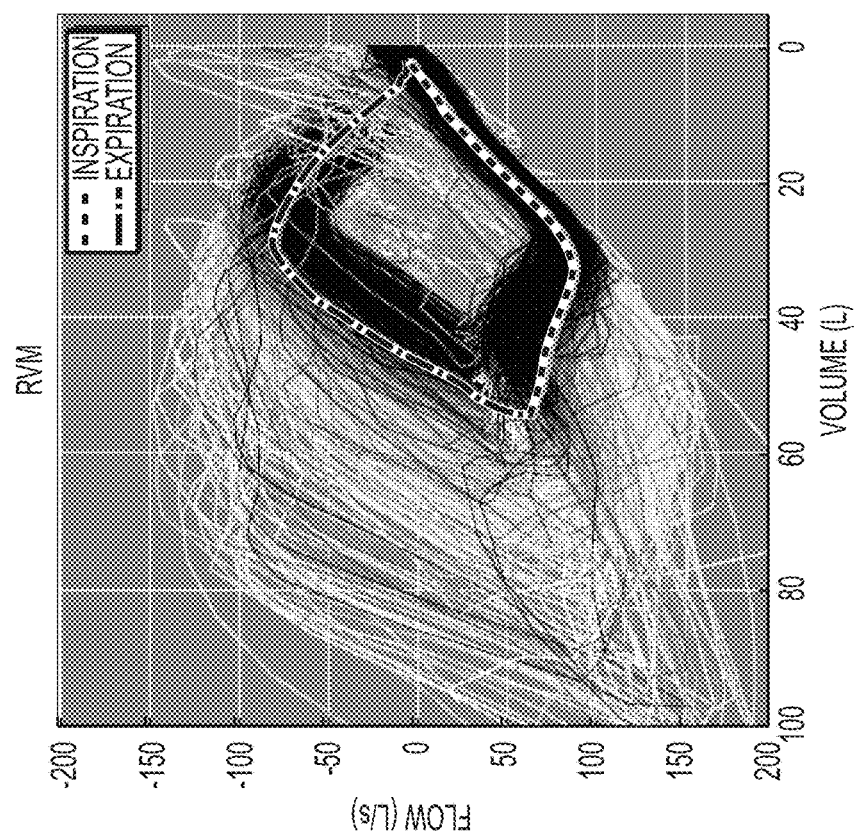
Figure 6A:
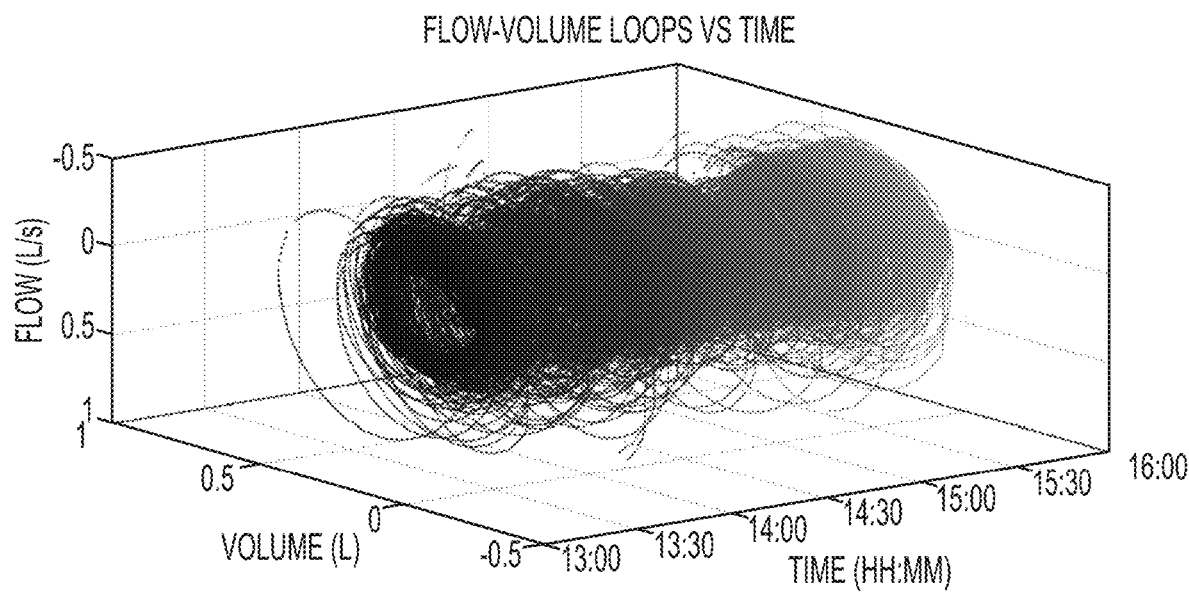
FIG. 6A A sequence of tidal volume FVLs plotted against time, creating a "tunnel". The shape of this tunnel can be used to aid in assessment of respiratory status, respiratory performance, alterations in respiration from medication or other therapy, response to specific respiratory stimuli, monitoring of respiration over time during daily life or during specifically designated activities, diagnosis of disease and monitoring of therapeutics.
Figure 6B:
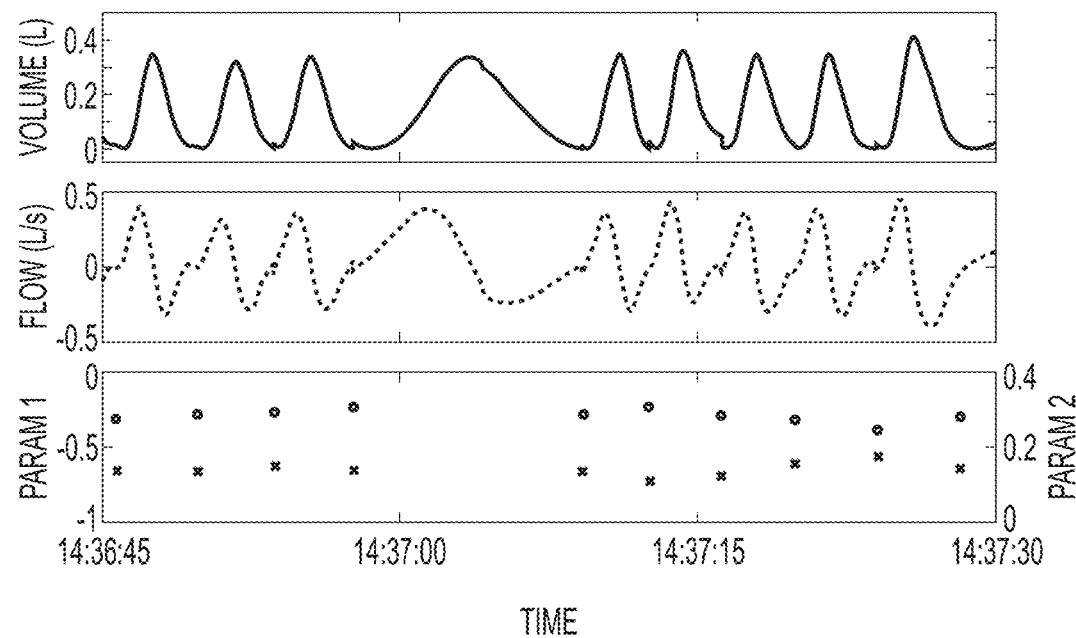
FIG. 6B Each FVL is composed of the respiratory volume (top) and flow (middle) recordings. Various parameters can be calculated based on the FVLs, volume, flow, or temporal relationships between those. These parameters can then be displayed on a graph (bottom) or used to trigger an alarm system or used for diagnosis of respiratory disease.

48 subjects (15 females/33 males, age: 46.1±14.3 years; BMI: 27.6±6.2 kg/m2, mean±SD) completed the study. Respiratory rates for the normal, fast, and slow breathing trials were 12.6±0.6 min-1, 24.6±0.1 min-1, and 6.9±0.3 min-1 (mean±SEM), respectively. FIG. 4 depicts representative volume (top row), flow (middle row), and FVLs (bottom row) for normal, fast, and slow breathing trials. The FVLs display all breaths during the breathing trials as well as the average inspiratory (dashed) and expiratory (dash-dot) curves. For the normal breathing trial (left column), the FVL has a convex shape with a steady flow during the second half of the expiratory limb. The FVLs during the fast breathing trial are elliptical with a major axis with a steep slope. During the slow breathing protocol, a concave expiratory limb is observed near the end of expiration indicating an expiratory flow limitation which is observed in patients with obstructive lung diseases such as COPD.

The study demonstrated the capability of the non-invasive RVM in generating continuous tidal FVLs in healthy volunteers. Distinctive shapes of the FVLs when the subjects varied their respiratory rate were observed. While this study was done with healthy volunteers, the results indicate that FVLs generated by the RVM can identify abnormalities observed in patients with lung diseases. The RVM eliminates the need for a spirometer and vastly expands the potential applications in which FVL can be measured.

Example

Monitoring TBFVLs in Healthy Volunteers and Patients Recovering from Surgery

As part of an IRB approved study, 20 healthy adult volunteers were simultaneously monitored with a RVM and a pneumotachometer (while breathing at rest for 10 minutes. Another 20 patients recovering from abdominal surgery were monitored with only the RVM for up to 48 hours on a hospital floor. TBFVLs and metrics were recorded for both devices including: respiratory rate (RR), tidal volume (TV), inspiratory time (tI), expiratory time (tE), inspiratory and expiratory ratio (tI/tE), duty cycle (tI/tTot) and inspiratory and expiratory flow ratio at 50% tidal volume (IE50). Bland Altman accuracy of TBFVL metrics were calculated for volunteers using the pneumotachometer as the standard. TBFVLs were visualized over time for post-operative patients.

Bland Altman analysis showed that the differences between the RVM and pneumotachometer was small and clinically irrelevant for TV and RR, with a root mean square error (RMSE) of 9.9% and 1.5%, respectively. The RMSE for tI and tE measured for each breath were 11.8% and 10.9%, respectively. The RMSE for ratios tI/tE, tI/tTot and IE50 were 15.3%, 10.8% and 17.0% respectively. In order to visually detect changes in TBFVLs over extended monitoring periods from post-operative patients, breath by breath TBFVLs were also visualized as 3D plots over time. Sample traces of breath by breath volume, flow, peak tidal expiratory flow, and volume at peak tidal expiratory flow were also plotted against time.

The RVM generated TBFVLs that are similar in morphology compared to spirometry without the need for patient cooperation or inconvenient instrumentation. Therefore, the RVM can be used to non-invasively monitor TBFVLs and provide clinically relevant pulmonary metrics for extended durations. The FVLs and metrics generated by the RVM can be used to detect anomalies in breathing and diagnose both adult and pediatric patients, either at the bedside or in the pulmonary function test laboratory.

Other embodiments and uses of the invention will be apparent to those skilled in the art from consideration of the specification and practice of the invention disclosed herein. While multiple embodiments are described herein elements from one embodiment may be used in another embodiment and several embodiments can be combined into a single embodiment. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A method of acquiring and displaying flow-volume loops of a patient and variability of the flow-volume loops across measured breaths, comprising on an electrical impedance monitor:
    obtaining a physiological dataset of the patient through impedance probes placed externally on the patient, wherein the physiological dataset is based on changes in impedance of a torso of the patient;
    applying a smoothing and curve fitting algorithm to the physiological dataset on a processor to obtain real-time data and calculate volume and flow parameters;
    creating a continuous spring-shaped visualization of connected flow-volume loops based on the volume and flow parameters on the processor;
    outputting a plot of the continuous spring-shaped visualization on a display, wherein the plot forms a tunnel of flow-volume loops indicating changes in the volume and flow parameters, and indicating changes in respiratory rate over time; and
    adjusting a treatment in real-time based on changes in the flow-volume loops.

2. The method of claim 1, further comprising, pairing flow volume loops with metrics of tidal volume and respiratory rate.

3. The method of claim 1, further comprising applying matching algorithms on the processor to identify normal flow-volume loops and flow-volume loops that indicate likely pathological states or states of altered physiology.

4. The method of claim 1, further comprising tracking and updating flow-volume loops on the processor to identify response to at least one of treatment, change in activity, change in exercise regimen and therapeutic manipulations.

5. The method of claim 4, further comprising displaying on the display at least one indication of the effectiveness of at least one of treatment, change in activity, change in exercise regimen, and therapeutic manipulations.

6. The method of claim 1, wherein the electrical impedance monitor, the processor and the display are coupled over a distance by a communication network.

7. The method of claim 1, wherein the physiological dataset is a respiratory dataset.

8. The method of claim 1, wherein the physiologic dataset is a cardiac dataset.

9. The method of claim 1, wherein the smoothing and curve fitting algorithms are one of a moving average algorithm, a digital filter algorithm, and fitting via iterative, error reducing learning algorithm.

10. The method of claim 1, wherein multiple flow-volume loops are overlaid on the displayed.

11. The method of claim 10, wherein the overlaid loops are integrated into a representative loop.

12. The method of claim 1, wherein multiple flow-volume loops are graphed adjacently to display differences between the flow-volume loops.

13. The method of claim 12, wherein the adjacently graphed flow-volume loops are displayed in a spiral configuration.

14. The method of claim 1, wherein a flow-volume loop is segmented into separate components and each component is analyzed individually.

15. The method of claim 1, wherein an automated, unsupervised algorithm identifies flow-volume loops of interest via matching algorithms.

16. The method of claim 1, further comprising creating a database wherein diagnostic information related to flow-volume loops are continually updated and classified according to clinically relevant respiratory-system related diagnoses.

17. The method of claim 1, further comprising creating a database wherein diagnostic information related to flow-volume loops are continually updated and classified according to clinically relevant cardiac-system related diagnoses.

18. The method of claim 1, further comprising creating a flow-volume template to facilitate algorithmic identification of continuously generated flow-volume loops that match or fall outside the template.

19. The method of claim 1, wherein the flow-volume loops are collected from a non-intubated patient.

20. The method of claim 1, wherein the flow-volume loops are paired with ongoing volume measurements corrected for patient parameters.

21. The method of claim 1, wherein the flow-volume loops are paired with ongoing respiratory rate evaluation.

22. The method of claim 1, wherein the flow-volume loops are paired with ongoing heart rate evaluation.

23. The method of claim 1, wherein the flow-volume loops are paired with both ongoing volume and ongoing respiratory rate evaluation.

24. The method of claim 1, wherein the flow-volume loops are paired with both ongoing stroke volume and ongoing heart rate evaluation.

25. The method of claim 1, further comprising classifying the flow-volume loops for analysis, interpretation and display based on respiratory rate and/or volume measurements.

26. The method of claim 1, further comprising interpreting the flow-volume loops for diagnosis, response to changes in physiology, response to interventions based on respiratory rate and/or volume measurements.

27. The method of claim 1, further comprising triggering at least one of an alarm, an alert, or an annotation in a record if one or more flow-volume loops are outside of predetermined parameters or if one or more flow-volume loops deviate from previous flow-volume loops by predetermined deviation.

28. A system of acquiring and displaying flow-volume loops of a patient and variability of the flow-volume loops across measured breaths, comprising:
an electrical impedance monitor coupled to impedance probes and adapted to obtain a physiological dataset of the patient that acquires data through the impedance probes adapted to be placed externally on the patient, wherein the physiological dataset is based on changes in impedance of a torso of the patient;
the electrical impedance monitor comprising:
a processor adapted to apply a smoothing and curve fitting algorithm to the physiological dataset to obtain real-time data and calculate volume and flow parameters at a plurality of time instances;
wherein the processor is adapted to create a continuous spring-shaped visualization of connected flow-volume loops based on the volume and flow parameters; and
a display adapted to output a plot of the continuous spring-shaped visualization, wherein the plot forms a tunnel of flow-volume loops indicating changes in the volume and flow parameters, and indicating changes in respiratory rate over time; and
wherein a treatment is adjusted in real-time based on changes in the flow-volume loops.

29. The system of claim 28, wherein the processor pairs flow volume loops with metrics of tidal volume and respiratory rate.

30. The system of claim 28, wherein the processor applies matching algorithms to identify normal flow-volume loops and flow-volume loops that indicate likely pathological states or states of altered physiology.

31. The system of claim 28, wherein the processor tracks and updates flow-volume loops to identify response to at least one of treatment, change in activity, change in exercise regimen and therapeutic manipulations.

32. The system of claim 31, wherein the display displays at least one indication of the effectiveness of at least one of treatment, change in activity, change in exercise regimen, and therapeutic manipulations.

33. The system of claim 28, wherein the electrical impedance monitor, the processor and the display device are coupled over a distance by a communication network.

34. The system of claim 28, wherein the physiological dataset is a respiratory dataset.

35. The system of claim 28, wherein the physiologic dataset is a cardiac dataset.

36. The system of claim 28, wherein the smoothing and curve fitting algorithms are one of a moving average algorithm, a digital filter algorithm, and fitting via iterative, error reducing learning algorithm.

37. The system of claim 28, wherein multiple flow-volume loops are overlaid on the displayed.

38. The system of claim 37, wherein the overlaid loops are integrated into a representative loop.

39. The system of claim 28, wherein multiple flow-volume loops are graphed adjacently to display differences between the flow-volume loops.

40. The system of claim 39, wherein the adjacently graphed flow-volume loops are displayed in a spiral configuration.

41. The system of claim 28, wherein a flow-volume loop is segmented into separate components and each component is analyzed in individually.

42. The system of claim 28, wherein an automated, unsupervised algorithm identifies flow-volume loops of interest via matching algorithms.

43. The system of claim 28, further comprising a database wherein diagnostic information related to flow-volume loops are continually updated and classified according to clinically relevant respiratory-system related diagnoses.

44. The system of claim 28, further comprising a database wherein diagnostic information related to flow-volume loops are continually updated and classified according to clinically relevant cardiac-system related diagnoses.

45. The system of claim 28, wherein the processor creates a flow-volume template to facilitate algorithmic identification of continuously generated flow-volume loops that match or fall outside the template.

46. The system of claim 28, wherein the flow-volume loops are collected from a non-intubated patient.

47. The system of claim 28, wherein the flow-volume loops are paired with ongoing volume measurements corrected for patient parameters.

48. The system of claim 28, wherein the flow-volume loops are paired with ongoing respiratory rate evaluation.

49. The system of claim 28, wherein the flow-volume loops are paired with ongoing heart rate evaluation.

50. The system of claim 28, wherein the flow-volume loops are paired with both ongoing volume and ongoing respiratory rate evaluation.

51. The system of claim 28, wherein the flow-volume loops are paired with both ongoing stroke volume and ongoing heart rate evaluation.

52. The system of claim 28, wherein the processor classifies the flow-volume loops for analysis, interpretation and display based on respiratory rate and/or volume measurements.

53. The system of claim 28, wherein the processor interprets the flow-volume loops for diagnosis, response to changes in physiology, response to interventions based on respiratory rate and/or volume measurements.

54. The system of claim 28, further comprising at least one of an alarm, an alert, or an annotation in a record that is triggered if one or more flow-volume loops are outside of predetermined parameters or if one or more flow-volume loops deviate from previous flow-volume loops by predetermined deviation.

\* \* \* \* \*